United States Patent
Hatch et al.

(10) Patent No.: US 8,690,898 B2
(45) Date of Patent: Apr. 8, 2014

(54) SUTURE PASSING SURGICAL INSTRUMENT

(75) Inventors: Laird L. Hatch, Cave Creek, AZ (US);
James J. Sullivan, Shrewsbury, MA (US)

(73) Assignee: Smith & Nephew, Inc., Andover, MA (US)

( * ) Notice: Subject to any disclaimer, the term of this patent is extended or adjusted under 35 U.S.C. 154(b) by 2418 days.

(21) Appl. No.: 11/165,163

(22) Filed: Jun. 24, 2005

(65) Prior Publication Data
US 2005/0234479 A1    Oct. 20, 2005

Related U.S. Application Data

(63) Continuation of application No. 10/151,812, filed on May 22, 2002, now Pat. No. 6,984,237.

(51) Int. Cl.
*A61B 17/04* (2006.01)
*A61B 17/06* (2006.01)
*A61B 17/28* (2006.01)

(52) U.S. Cl.
USPC .................. 606/144; 606/148; 606/205

(58) Field of Classification Search
USPC ............... 606/205, 139, 144–148; 112/169
See application file for complete search history.

(56) References Cited

U.S. PATENT DOCUMENTS

| | | |
|---|---|---|
| 349,791 A | 9/1886 | Gibboney, Jr. |
| 373,372 A | 11/1887 | King |
| 421,919 A | 2/1890 | Fergen |
| 424,518 A | 4/1890 | Van Norman |
| 652,175 A | 6/1900 | Felson |
| 659,422 A | 10/1900 | Shidler |
| 671,337 A | 4/1901 | Gibson |
| 786,000 A | 3/1905 | Botkin |
| 854,147 A | 5/1907 | Carillon |
| 919,138 A | 4/1909 | Drake et al. |
| 1,009,065 A | 11/1911 | Hahn et al. |
| 1,066,317 A | 7/1913 | Pirnat |

(Continued)

FOREIGN PATENT DOCUMENTS

| | | |
|---|---|---|
| DE | 245 576 | 4/1912 |
| DE | 321755 | 6/1957 |

(Continued)

OTHER PUBLICATIONS

Office Action issued in parent U.S. Appl. No. 10/151,812 dated May 18, 2004.

(Continued)

*Primary Examiner* — Corrine M McDermott
*Assistant Examiner* — Mark Mashack
(74) *Attorney, Agent, or Firm* — Pierce Atwood LLP; Joseph M. Maraia

(57) ABSTRACT

A surgical instrument includes first and second members configured to receive tissue therebetween. The first member is adapted to receive suture, the second member is coupled to the first member, and a grasper coupled to the second member engages the suture received by the first member. A method of passing suture includes loading suture into a first member of a suture passing surgical instrument, stabilizing tissue between the first member and a second member of the surgical instrument, passing suture through tissue via the first member of the surgical instrument, holding the passed suture via a suture grasper of the surgical instrument, and removing the first member from the tissue.

26 Claims, 20 Drawing Sheets

(56) References Cited

U.S. PATENT DOCUMENTS

| | | |
|---|---|---|
| 1,293,565 A | 2/1919 | Smit |
| 1,449,087 A | 3/1923 | Bugbee |
| 1,464,832 A | 8/1923 | Richardson |
| 1,579,379 A | 4/1926 | Marbel |
| 1,635,066 A | 7/1927 | Wells |
| 1,641,077 A | 8/1927 | Fouguet |
| 1,656,467 A | 1/1928 | Blake |
| 1,815,725 A | 7/1931 | Pilling et al. |
| 1,822,330 A | 9/1931 | Ainslie |
| 1,855,546 A | 4/1932 | File |
| 1,856,721 A | 5/1932 | Nagelmann |
| 1,876,792 A | 9/1932 | Thompson |
| 1,933,024 A | 10/1933 | Nagelmann |
| 2,023,807 A | 12/1935 | Gruss et al. |
| 2,042,403 A | 5/1936 | Hrivnak |
| 2,065,659 A | 12/1936 | Cullen |
| 2,213,830 A | 9/1940 | Anastasi |
| 2,316,297 A | 4/1943 | Southerland et al. |
| 2,348,218 A | 5/1944 | Karle |
| 2,396,180 A | 7/1944 | Karle |
| 2,414,746 A | 7/1944 | Karle |
| 2,411,118 A | 11/1946 | Schuster |
| 2,414,882 A | 1/1947 | Longfellow |
| 2,434,133 A | 1/1948 | Volk |
| 2,577,240 A | 12/1951 | Findley |
| 2,579,192 A | 12/1951 | Kohl |
| 2,593,622 A | 4/1952 | Stanelle |
| 2,601,564 A | 6/1952 | Smith |
| 2,610,631 A | 9/1952 | Calicchio |
| 2,611,366 A | 9/1952 | Mull |
| 2,646,045 A | 7/1953 | Priestley |
| 2,738,790 A | 3/1956 | Todt et al. |
| 2,808,055 A | 10/1957 | Thayer |
| 2,880,728 A | 4/1959 | Rights |
| 2,895,478 A | 7/1959 | Post |
| 2,959,172 A * | 11/1960 | Held |
| 3,013,559 A | 12/1961 | Thomas |
| 3,036,482 A | 5/1962 | Kenworthy et al. |
| 3,073,311 A | 1/1963 | Tibbs et al. |
| 3,090,386 A | 5/1963 | Curtis |
| 3,139,089 A | 6/1964 | Schwerin |
| 3,349,772 A | 10/1967 | Rygg |
| 3,372,477 A | 3/1968 | Hoppe |
| 3,393,687 A | 7/1968 | Whitman |
| 3,417,752 A | 12/1968 | Butler |
| 3,470,834 A | 10/1969 | Bone |
| 3,470,875 A | 10/1969 | Johnson |
| 3,638,653 A | 2/1972 | Berry |
| 3,687,138 A | 8/1972 | Jarvik |
| 3,716,058 A | 2/1973 | Tanner, Jr. |
| 3,752,516 A | 8/1973 | Mumma |
| 3,763,860 A | 10/1973 | Clarke |
| 3,807,407 A | 4/1974 | Schweizer |
| 3,840,017 A | 10/1974 | Violante |
| 3,842,824 A | 10/1974 | Neufeld |
| 3,842,840 A | 10/1974 | Schweizer |
| 3,856,018 A | 12/1974 | Perisse et al. |
| 3,871,379 A | 3/1975 | Clarke |
| 3,890,975 A | 6/1975 | McGregor |
| 3,901,244 A | 8/1975 | Schweizer |
| 3,946,740 A | 3/1976 | Bassett |
| 3,980,177 A | 9/1976 | McGregor |
| 3,985,138 A | 10/1976 | Jarvik |
| 3,990,619 A | 11/1976 | Russell |
| 4,027,608 A | 6/1977 | Arbuckle |
| 4,064,881 A | 12/1977 | Meredith |
| 4,109,658 A | 8/1978 | Hughes |
| 4,161,951 A * | 7/1979 | Scanlan, Jr. .................... 606/145 |
| 4,164,225 A | 8/1979 | Johnson et al. |
| 4,169,476 A | 10/1979 | Hiltebrandt |
| 4,224,947 A | 9/1980 | Fukuda |
| 4,235,238 A | 11/1980 | Ogiu et al. |
| 4,236,470 A | 12/1980 | Stenson |
| 4,312,337 A | 1/1982 | Donohue |
| 4,326,531 A | 4/1982 | Shimonaka |
| 4,345,600 A | 8/1982 | Rothfuss |
| 4,345,601 A | 8/1982 | Fukuda |
| 4,373,530 A | 2/1983 | Kilejian |
| 4,384,406 A | 5/1983 | Tischlinger |
| 4,414,466 A | 11/1983 | Fischer et al. |
| 4,414,908 A | 11/1983 | Eguchi et al. |
| 4,417,532 A | 11/1983 | Yasukata |
| 4,423,729 A | 1/1984 | Gray |
| 4,440,171 A | 4/1984 | Nomoto et al. |
| 4,441,497 A | 4/1984 | Paudler |
| 4,448,194 A | 5/1984 | DiGiovanni et al. |
| 4,463,753 A | 8/1984 | Gustilo |
| 4,471,781 A | 9/1984 | Di Giovanni et al. |
| 4,493,323 A | 1/1985 | Albright et al. |
| 4,500,024 A | 2/1985 | DiGiovanni et al. |
| 4,509,516 A | 4/1985 | Richmond |
| 4,512,344 A | 4/1985 | Barber |
| 4,535,768 A | 8/1985 | Hourahane et al. |
| 4,553,543 A | 11/1985 | Amarasinghe |
| 4,553,544 A | 11/1985 | Nomoto et al. |
| 4,557,265 A | 12/1985 | Andersson |
| 4,574,805 A | 3/1986 | Lerner |
| 4,580,563 A | 4/1986 | Gross |
| 4,590,929 A | 5/1986 | Klein |
| 4,596,249 A | 6/1986 | Freda et al. |
| 4,602,635 A | 7/1986 | Mulhollan et al. |
| 4,621,639 A | 11/1986 | Transue et al. |
| 4,621,640 A | 11/1986 | Mulhollan et al. |
| 4,633,869 A | 1/1987 | Schmeiding |
| 4,636,121 A | 1/1987 | Miller |
| 4,641,652 A | 2/1987 | Hutterer et al. |
| 4,643,178 A | 2/1987 | Nastari et al. |
| 4,660,559 A | 4/1987 | McGregor et al. |
| 4,662,068 A | 5/1987 | Polonsky |
| 4,716,893 A | 1/1988 | Fischer et al. |
| 4,723,546 A | 2/1988 | Zagorski |
| 4,724,840 A | 2/1988 | McVay et al. |
| 4,739,751 A | 4/1988 | Sapega et al. |
| 4,741,330 A | 5/1988 | Hayhurst |
| 4,778,468 A | 10/1988 | Hunt et al. |
| 4,779,616 A | 10/1988 | Johnson |
| 4,781,190 A | 11/1988 | Lee |
| 4,787,377 A | 11/1988 | Laboureau |
| 4,790,312 A | 12/1988 | Capuano, Sr. et al. |
| 4,836,205 A | 6/1989 | Barrett |
| 4,846,799 A | 7/1989 | Tanaka et al. |
| 4,870,957 A | 10/1989 | Goble et al. |
| 4,871,289 A | 10/1989 | Choiniere |
| 4,881,537 A | 11/1989 | Henning |
| 4,884,572 A | 12/1989 | Bays et al. |
| 4,890,615 A | 1/1990 | Caspari et al. |
| 4,895,148 A | 1/1990 | Bays et al. |
| 4,899,743 A | 2/1990 | Nicholson et al. |
| 4,915,107 A | 4/1990 | Rebuffat et al. |
| 4,923,461 A | 5/1990 | Caspari et al. |
| 4,926,860 A | 5/1990 | Stice et al. |
| 4,932,961 A | 6/1990 | Wong et al. |
| 4,935,027 A | 6/1990 | Yoon |
| 4,950,285 A | 8/1990 | Wilk |
| 4,955,897 A | 9/1990 | Ship |
| 4,957,498 A | 9/1990 | Caspari et al. |
| 4,961,741 A | 10/1990 | Hayhurst |
| 4,976,715 A | 12/1990 | Bays et al. |
| 5,002,563 A | 3/1991 | Pyka et al. |
| 5,013,292 A | 5/1991 | Lemay |
| 5,015,250 A | 5/1991 | Foster |
| 5,026,350 A | 6/1991 | Tanaka et al. |
| 5,037,422 A | 8/1991 | Hayhurst et al. |
| 5,037,433 A | 8/1991 | Wilk et al. |
| 5,053,047 A | 10/1991 | Yoon |
| 5,059,201 A | 10/1991 | Asnis |
| 5,084,058 A | 1/1992 | Li |
| 5,085,661 A | 2/1992 | Moss |
| 5,087,263 A | 2/1992 | Li |
| 5,100,415 A | 3/1992 | Hayhurst |
| 5,100,418 A | 3/1992 | Yoon et al. |
| 5,100,421 A | 3/1992 | Christoudias |
| 5,120,318 A | 6/1992 | Nallapareddy |
| 5,123,913 A | 6/1992 | Wilk et al. |

(56) References Cited

U.S. PATENT DOCUMENTS

| | | |
|---|---|---|
| 5,129,912 A | 7/1992 | Noda et al. |
| 5,133,723 A | 7/1992 | Li et al. |
| 5,149,329 A | 9/1992 | Richardson |
| 5,152,764 A | 10/1992 | Goble |
| 5,152,769 A | 10/1992 | Baber |
| 5,152,790 A | 10/1992 | Rosenberg et al. |
| 5,163,946 A | 11/1992 | Li |
| 5,174,087 A | 12/1992 | Bruno |
| 5,176,691 A | 1/1993 | Pierce |
| 5,178,629 A | 1/1993 | Kammerer |
| 5,181,919 A | 1/1993 | Bergman et al. |
| 5,188,636 A | 2/1993 | Fedotov |
| 5,192,287 A | 3/1993 | Fournier et al. |
| 5,201,743 A | 4/1993 | Haber et al. |
| 5,201,744 A | 4/1993 | Jones |
| 5,211,650 A | 5/1993 | Noda |
| 5,217,471 A | 6/1993 | Burkhart |
| 5,217,486 A | 6/1993 | Rice et al. |
| 5,219,358 A | 6/1993 | Bendel et al. |
| 5,222,508 A | 6/1993 | Contarini |
| 5,222,962 A | 6/1993 | Burkhart |
| 5,222,976 A | 6/1993 | Yoon et al. |
| 5,222,977 A | 6/1993 | Esser |
| 5,224,955 A | 7/1993 | West |
| 5,234,443 A | 8/1993 | Phan et al. |
| 5,234,444 A | 8/1993 | Christoudias |
| 5,242,458 A | 9/1993 | Bendel et al. |
| 5,248,231 A | 9/1993 | Denham et al. |
| 5,250,054 A | 10/1993 | Li |
| 5,250,055 A | 10/1993 | Moore et al. |
| 5,254,126 A | 10/1993 | Filipi et al. |
| 5,257,637 A | 11/1993 | El Gazayerli |
| 5,259,846 A | 11/1993 | Granger et al. |
| 5,261,917 A | 11/1993 | Hasson et al. |
| 5,266,075 A | 11/1993 | Clark et al. |
| 5,269,783 A | 12/1993 | Sander |
| 5,269,786 A | 12/1993 | Morgan |
| 5,269,791 A | 12/1993 | Mayzels et al. |
| 5,273,024 A | 12/1993 | Menon et al. |
| 5,275,613 A | 1/1994 | Haber et al. |
| 5,281,234 A | 1/1994 | Wilk et al. |
| 5,282,809 A | 2/1994 | Kammerer et al. |
| 5,292,327 A | 3/1994 | Dodd et al. |
| 5,304,184 A | 4/1994 | Hathaway et al. |
| 5,304,185 A | 4/1994 | Taylor |
| 5,306,280 A | 4/1994 | Bregen et al. |
| 5,308,353 A | 5/1994 | Feurrier |
| 5,312,422 A | 5/1994 | Trott |
| 5,318,577 A | 6/1994 | Li |
| 5,318,579 A | 6/1994 | Chow |
| 5,320,632 A | 6/1994 | Heidmueller |
| 5,327,896 A | 7/1994 | Schmieding |
| 5,334,198 A | 8/1994 | Hart et al. |
| 5,356,419 A | 10/1994 | Chow |
| 5,364,408 A | 11/1994 | Gordon |
| 5,364,409 A | 11/1994 | Kuwabara et al. |
| 5,368,601 A | 11/1994 | Sauer et al. |
| 5,368,606 A | 11/1994 | Marlow et al. |
| 5,372,604 A | 12/1994 | Trott |
| 5,374,275 A | 12/1994 | Bradley |
| 5,376,096 A | 12/1994 | Foster |
| 5,382,257 A | 1/1995 | Lewis et al. |
| 5,387,221 A | 2/1995 | Bisgaard |
| 5,387,227 A | 2/1995 | Grice |
| 5,389,103 A | 2/1995 | Melzer et al. |
| 5,391,170 A | 2/1995 | McGuire et al. |
| 5,391,173 A | 2/1995 | Wilk |
| 5,393,302 A | 2/1995 | Clark et al. |
| 5,397,325 A | 3/1995 | Della Badia et al. |
| 5,403,328 A | 4/1995 | Shallman |
| 5,403,329 A | 4/1995 | Hinchcliffe |
| 5,409,494 A | 4/1995 | Morgan |
| 5,417,699 A | 5/1995 | Klein et al. |
| 5,417,701 A | 5/1995 | Holmes |
| 5,423,837 A | 6/1995 | Mericle et al. |
| 5,425,733 A | 6/1995 | Schmieding |
| 5,431,678 A | 7/1995 | Rogers |
| 5,433,722 A | 7/1995 | Sharpe et al. |
| 5,439,467 A | 8/1995 | Benderev et al. |
| 5,439,474 A | 8/1995 | Li |
| 5,441,502 A | 8/1995 | Bartlett |
| 5,441,507 A | 8/1995 | Wilk |
| 5,449,367 A | 9/1995 | Kadry |
| 5,454,823 A | 10/1995 | Richardson et al. |
| 5,456,246 A | 10/1995 | Schmieding et al. |
| 5,462,562 A | 10/1995 | Elkus |
| 5,464,425 A | 11/1995 | Skiba |
| 5,466,243 A | 11/1995 | Schmieding et al. |
| 5,470,338 A | 11/1995 | Whitfield et al. |
| 5,474,565 A | 12/1995 | Trott |
| 5,476,470 A | 12/1995 | Fitzgibbons, Jr. |
| 5,478,344 A | 12/1995 | Stone et al. |
| 5,478,345 A | 12/1995 | Stone et al. |
| 5,480,406 A | 1/1996 | Nolan et al. |
| 5,496,331 A | 3/1996 | Xu et al. |
| 5,496,335 A | 3/1996 | Thomason et al. |
| 5,499,991 A | 3/1996 | Garman et al. |
| 5,501,688 A | 3/1996 | Whiteside et al. |
| 5,501,692 A | 3/1996 | Riza |
| D368,776 S | 4/1996 | Toy et al. |
| 5,505,735 A | 4/1996 | Li |
| 5,507,755 A | 4/1996 | Gresl et al. |
| 5,507,757 A | 4/1996 | Sauer et al. |
| 5,520,696 A | 5/1996 | Wenstrom, Jr. |
| 5,520,703 A | 5/1996 | Essig et al. |
| 5,522,820 A | 6/1996 | Caspari et al. |
| 5,527,321 A | 6/1996 | Hinchliffe |
| 5,527,322 A | 6/1996 | Klein et al. |
| 5,540,705 A | 7/1996 | Meade et al. |
| 5,545,170 A | 8/1996 | Hart |
| 5,549,613 A | 8/1996 | Goble et al. |
| 5,549,618 A | 8/1996 | Fleenor et al. |
| 5,549,636 A | 8/1996 | Li |
| 5,554,171 A | 9/1996 | Gatturna et al. |
| 5,562,683 A | 10/1996 | Chan |
| 5,562,686 A | 10/1996 | Sauer et al. |
| 5,562,687 A | 10/1996 | Chan |
| 5,562,696 A | 10/1996 | Nobles et al. |
| 5,565,122 A | 10/1996 | Zinnbauer et al. |
| 5,569,269 A | 10/1996 | Hart et al. |
| 5,569,299 A | 10/1996 | Dill et al. |
| 5,569,301 A | 10/1996 | Granger et al. |
| 5,571,090 A | 11/1996 | Sherts |
| 5,573,542 A | 11/1996 | Stevens |
| 5,575,801 A | 11/1996 | Habermeyer et al. |
| 5,578,044 A | 11/1996 | Gordon et al. |
| 5,584,835 A | 12/1996 | Greenfield |
| 5,586,986 A | 12/1996 | Hinchliffe |
| 5,591,179 A | 1/1997 | Edelstein |
| 5,591,180 A | 1/1997 | Hinchliffe |
| 5,601,557 A | 2/1997 | Hayhurst |
| 5,601,571 A | 2/1997 | Moss |
| 5,603,718 A | 2/1997 | Xu |
| 5,607,435 A | 3/1997 | Sachdeva et al. |
| 5,618,290 A | 4/1997 | Toy et al. |
| 5,618,304 A | 4/1997 | Hart et al. |
| 5,626,588 A | 5/1997 | Sauer et al. |
| 5,626,590 A | 5/1997 | Wilk |
| 5,630,825 A | 5/1997 | de la Torre et al. |
| 5,632,748 A | 5/1997 | Beck, Jr. et al. |
| 5,632,751 A | 5/1997 | Piraka |
| 5,643,266 A | 7/1997 | Li |
| 5,643,289 A * | 7/1997 | Sauer et al. ............ 606/139 |
| 5,643,292 A | 7/1997 | Hart |
| 5,645,552 A | 7/1997 | Sherts |
| 5,649,939 A | 7/1997 | Reddick |
| 5,653,716 A | 8/1997 | Malo et al. |
| 5,658,299 A | 8/1997 | Hart |
| 5,662,658 A | 9/1997 | Wenstrom, Jr. |
| 5,662,665 A | 9/1997 | Ludwick |
| 5,665,096 A * | 9/1997 | Yoon ............................ 606/139 |
| 5,667,526 A | 9/1997 | Levin |
| 5,674,229 A | 10/1997 | Tovey et al. |
| 5,674,230 A | 10/1997 | Tovey et al. |

(56) References Cited

U.S. PATENT DOCUMENTS

| | | |
|---|---|---|
| 5,681,333 A | 10/1997 | Burkhart et al. |
| 5,690,652 A | 11/1997 | Wurster et al. |
| 5,690,653 A | 11/1997 | Richardson et al. |
| 5,690,677 A | 11/1997 | Schmieding et al. |
| 5,693,061 A | 12/1997 | Pierce et al. |
| 5,693,071 A | 12/1997 | Gorecki et al. |
| 5,695,522 A | 12/1997 | LeMaire, III et al. |
| 5,697,950 A | 12/1997 | Fucci et al. |
| 5,700,273 A | 12/1997 | Buelna et al. |
| 5,707,379 A | 1/1998 | Fleenor et al. |
| 5,709,694 A | 1/1998 | Greenberg et al. |
| 5,713,908 A | 2/1998 | Jameel et al. |
| 5,728,107 A | 3/1998 | Zlock et al. |
| 5,728,112 A | 3/1998 | Yoon |
| 5,728,113 A | 3/1998 | Sherts |
| 5,728,135 A | 3/1998 | Bregen et al. |
| 5,730,747 A | 3/1998 | Ek et al. |
| 5,735,862 A | 4/1998 | Jennings et al. |
| 5,741,278 A | 4/1998 | Stevens |
| 5,746,751 A | 5/1998 | Sherts |
| 5,746,753 A | 5/1998 | Sullivan et al. |
| 5,749,879 A | 5/1998 | Middleman et al. |
| 5,752,964 A | 5/1998 | Mericle |
| 5,755,728 A | 5/1998 | Maki |
| 5,759,188 A | 6/1998 | Yoon |
| 5,766,183 A | 6/1998 | Sauer |
| 5,766,186 A | 6/1998 | Faraz et al. |
| 5,776,152 A | 7/1998 | Sekons |
| 5,792,152 A | 8/1998 | Klein et al. |
| 5,797,927 A | 8/1998 | Yoon |
| 5,800,447 A | 9/1998 | Wenstrom, Jr. |
| 5,810,848 A | 9/1998 | Hayhurst |
| 5,810,852 A | 9/1998 | Greenberg et al. |
| 5,814,052 A | 9/1998 | Nakao et al. |
| 5,814,054 A | 9/1998 | Kortenbach et al. |
| 5,814,069 A | 9/1998 | Schulze et al. |
| 5,817,107 A | 10/1998 | Schaller |
| 5,817,111 A | 10/1998 | Riza |
| 5,824,009 A | 10/1998 | Fukuda et al. |
| 5,826,776 A | 10/1998 | Schulze et al. |
| 5,827,298 A | 10/1998 | Hart et al. |
| 5,827,299 A | 10/1998 | Thomason et al. |
| 5,830,220 A | 11/1998 | Wan et al. |
| 5,833,697 A | 11/1998 | Ludwick |
| 5,836,955 A | 11/1998 | Buelna et al. |
| 5,843,084 A | 12/1998 | Hart et al. |
| 5,843,099 A | 12/1998 | Nichols et al. |
| 5,843,100 A | 12/1998 | Meade |
| 5,846,254 A | 12/1998 | Schulze et al. |
| 5,855,311 A | 1/1999 | Hamblin et al. |
| 5,860,983 A | 1/1999 | Wenstrom, Jr. |
| 5,860,990 A | 1/1999 | Nobles et al. |
| 5,860,992 A | 1/1999 | Daniel et al. |
| 5,868,749 A | 2/1999 | Reed |
| 5,871,488 A | 2/1999 | Tovey et al. |
| 5,871,490 A | 2/1999 | Schulze et al. |
| 5,876,412 A | 3/1999 | Piraka |
| 5,879,371 A | 3/1999 | Gardiner et al. |
| 5,893,878 A | 4/1999 | Pierce |
| 5,895,393 A | 4/1999 | Pagedas |
| 5,895,395 A * | 4/1999 | Yeung .............. 606/144 |
| 5,897,563 A | 4/1999 | Yoon et al. |
| 5,897,564 A | 4/1999 | Schulze et al. |
| 5,897,572 A | 4/1999 | Schulsinger et al. |
| 5,897,574 A | 4/1999 | Bonutti |
| 5,899,911 A | 5/1999 | Carter |
| 5,904,692 A | 5/1999 | Steckel et al. |
| 5,908,426 A | 6/1999 | Pierce |
| 5,908,428 A * | 6/1999 | Scirica et al. .............. 606/139 |
| 5,910,148 A | 6/1999 | Reimels et al. |
| 5,918,604 A | 7/1999 | Whelan |
| 5,919,199 A | 7/1999 | Mers Kelly et al. |
| 5,925,064 A | 7/1999 | Meyers et al. |
| 5,928,252 A | 7/1999 | Steadman et al. |
| 5,928,267 A | 7/1999 | Bonutti et al. |
| 5,928,268 A | 7/1999 | Butwell et al. |
| 5,931,844 A | 8/1999 | Thompson et al. |
| 5,935,149 A | 8/1999 | Ek |
| 5,938,668 A | 8/1999 | Scirica et al. |
| 5,941,439 A | 8/1999 | Kammerer et al. |
| 5,944,724 A | 8/1999 | Lizardi |
| 5,947,982 A | 9/1999 | Duran |
| 5,951,559 A | 9/1999 | Burkhart |
| 5,954,732 A | 9/1999 | Hart et al. |
| 5,954,733 A | 9/1999 | Yoon |
| 5,957,937 A | 9/1999 | Yoon |
| 5,964,773 A | 10/1999 | Greenstein |
| 5,968,047 A | 10/1999 | Reed |
| 5,980,538 A * | 11/1999 | Fuchs et al. .............. 606/145 |
| 5,980,557 A | 11/1999 | Iserin et al. |
| 5,984,932 A | 11/1999 | Yoon |
| 5,993,451 A | 11/1999 | Burkhart |
| 5,993,466 A | 11/1999 | Yoon |
| 5,993,467 A | 11/1999 | Yoon |
| 6,004,332 A | 12/1999 | Yoon et al. |
| 6,010,513 A | 1/2000 | Törmälä et al. |
| 6,017,358 A | 1/2000 | Yoon et al. |
| 6,024,747 A | 2/2000 | Kontos |
| 6,045,561 A | 4/2000 | Marshall et al. |
| 6,051,006 A | 4/2000 | Shluzas et al. |
| 6,059,800 A | 5/2000 | Hart et al. |
| 6,071,289 A | 6/2000 | Stefanchik et al. |
| 6,074,403 A | 6/2000 | Nord |
| 6,077,276 A | 6/2000 | Kontos |
| 6,080,180 A | 6/2000 | Yoon et al. |
| 6,086,601 A | 7/2000 | Yoon |
| 6,096,051 A | 8/2000 | Kortenbach et al. |
| 6,096,060 A | 8/2000 | Fitts et al. |
| 6,099,538 A | 8/2000 | Moses et al. |
| 6,102,920 A * | 8/2000 | Sullivan et al. .............. 606/147 |
| 6,117,144 A | 9/2000 | Nobles et al. |
| 6,126,665 A | 10/2000 | Yoon |
| 6,126,666 A | 10/2000 | Trapp et al. |
| 6,129,741 A | 10/2000 | Wurster et al. |
| 6,132,433 A | 10/2000 | Whelan |
| 6,143,004 A | 11/2000 | Davis et al. |
| 6,143,005 A | 11/2000 | Yoon et al. |
| 6,146,387 A | 11/2000 | Trott et al. |
| 6,159,224 A | 12/2000 | Yoon |
| 6,183,485 B1 | 2/2001 | Thomason et al. |
| 6,197,035 B1 | 3/2001 | Loubens et al. |
| 6,200,329 B1 | 3/2001 | Fung et al. |
| 6,217,592 B1 | 4/2001 | Freda et al. |
| 6,254,620 B1 | 7/2001 | Koh et al. |
| 6,277,132 B1 | 8/2001 | Brhel |
| 6,322,570 B1 | 11/2001 | Matsutani et al. |
| 6,332,889 B1 | 12/2001 | Sancoff et al. |
| 6,355,050 B1 | 3/2002 | Andreas et al. |
| 6,358,258 B1 | 3/2002 | Arcia et al. |
| 6,436,109 B1 | 8/2002 | Kontos |
| 6,443,963 B1 | 9/2002 | Baldwin et al. |
| 6,454,777 B1 | 9/2002 | Green |
| 6,461,366 B1 | 10/2002 | Seguin |
| 6,475,135 B1 | 11/2002 | Levy |
| 6,511,487 B1 * | 1/2003 | Oren et al. .............. 606/145 |
| 6,517,552 B1 | 2/2003 | Nord et al. |
| 6,551,330 B1 | 4/2003 | Bain et al. |
| 6,595,911 B2 | 7/2003 | LoVuolo |
| 6,599,298 B1 | 7/2003 | Forster et al. |
| 6,605,096 B1 | 8/2003 | Ritchart |
| 6,616,674 B2 | 9/2003 | Schmieding |
| 6,623,492 B1 | 9/2003 | Berube et al. |
| 6,638,283 B2 | 10/2003 | Thal |
| 6,679,895 B1 | 1/2004 | Sancoff et al. |
| 6,719,764 B1 | 4/2004 | Gellman et al. |
| 6,723,107 B1 | 4/2004 | Skiba et al. |
| 6,743,241 B2 | 6/2004 | Kerr |
| 6,770,084 B1 | 8/2004 | Bain et al. |
| 6,843,796 B2 | 1/2005 | Harari et al. |
| 6,896,686 B2 | 5/2005 | Webber |
| 6,984,237 B2 | 1/2006 | Hatch et al. |
| D523,554 S | 6/2006 | Weisel |
| D529,173 S | 9/2006 | Weisel |
| D530,421 S | 10/2006 | Topper et al. |

(56) References Cited

U.S. PATENT DOCUMENTS

| | | |
|---|---|---|
| 1,037,864 A1 | 9/2012 | Carlson et al. |
| 2002/0065526 A1 | 5/2002 | Oren et al. |
| 2002/0103493 A1 | 8/2002 | Thal |
| 2002/0111534 A1* | 8/2002 | Suzuki et al. ............... 600/102 |
| 2002/0128666 A1 | 9/2002 | Sancoff et al. |
| 2002/0138084 A1 | 9/2002 | Weber |
| 2002/0147456 A1* | 10/2002 | Diduch et al. ............... 606/144 |
| 2002/0173800 A1 | 11/2002 | Dreyfuss et al. |
| 2003/0023250 A1 | 1/2003 | Watschke et al. |
| 2003/0065337 A1* | 4/2003 | Topper et al. ............... 606/144 |
| 2003/0078599 A1 | 4/2003 | O'Quinn et al. |
| 2003/0078600 A1 | 4/2003 | O'Quinn et al. |
| 2003/0083695 A1 | 5/2003 | Morris et al. |
| 2003/0105474 A1 | 6/2003 | Bonutti |
| 2003/0144674 A1 | 7/2003 | Loubens et al. |
| 2003/0176874 A1 | 9/2003 | Sauer |
| 2003/0216756 A1 | 11/2003 | Klein et al. |
| 2003/0233106 A1 | 12/2003 | Dreyfuss |
| 2003/0233108 A1 | 12/2003 | Gellman et al. |
| 2004/0010273 A1 | 1/2004 | Diduch et al. |
| 2004/0073254 A1 | 4/2004 | Wyman et al. |
| 2004/0193185 A1 | 9/2004 | McBrayer |
| 2004/0199184 A1 | 10/2004 | Topper et al. |
| 2004/0249394 A1 | 12/2004 | Morris et al. |
| 2004/0260314 A1 | 12/2004 | Lizardi et al. |
| 2005/0043748 A1 | 2/2005 | Oren et al. |

FOREIGN PATENT DOCUMENTS

| | | |
|---|---|---|
| DE | 38 31 398 | 3/1990 |
| DE | 9109097 | 10/1991 |
| DE | 9112301 | 1/1992 |
| DE | 9203041 | 6/1992 |
| DE | 4 127 812 | 2/1993 |
| DE | 42 35 602 | 4/1994 |
| DE | 42 35 602 A1 | 4/1994 |
| EP | 0 591 991 | 4/1984 |
| EP | 0 119 967 | 9/1984 |
| EP | 0 140 557 | 9/1984 |
| EP | 0 136 262 A2 | 4/1985 |
| EP | 0 174 843 | 3/1986 |
| EP | 0 207 545 B1 | 1/1987 |
| EP | 0 315 371 B1 | 5/1989 |
| EP | 0 535 906 B1 | 4/1993 |
| EP | 0 574 707 A1 | 12/1993 |
| EP | 0 684 012 B1 | 11/1995 |
| EP | 0 778 004 A1 | 6/1997 |
| EP | 0 792 621 | 9/1997 |
| EP | 0 601 676 | 3/1999 |
| EP | 0 903 109 B1 | 3/1999 |
| EP | 1 159 920 A2 | 12/2001 |
| EP | 1 243 221 A2 | 9/2002 |
| GB | 630 693 | 10/1949 |
| GB | 2 081 099 | 2/1982 |
| GB | 2 260 704 A | 4/1993 |
| GB | 2 268 690 | 1/1994 |
| JP | 5-42161 | 2/1993 |
| JP | 06-063052 | 3/1994 |
| JP | 112 161 45 | 8/1999 |
| SU | 552077 | 7/1976 |
| WO | 89/10096 | 11/1989 |
| WO | 92/12674 | 8/1992 |
| WO | WO 94/28801 | 12/1994 |
| WO | 95/02363 | 1/1995 |
| WO | 95/08958 | 4/1995 |
| WO | WO 95/13021 | 5/1995 |
| WO | WO 96/09796 | 4/1996 |
| WO | WO 96/27331 | 9/1996 |
| WO | 96/39946 | 12/1996 |
| WO | 96/39948 | 12/1996 |
| WO | WO 97/41780 | 11/1997 |
| WO | WO 97/47246 | 12/1997 |
| WO | 98/30151 | 7/1998 |
| WO | 98/30152 | 7/1998 |
| WO | 98/30153 | 7/1998 |
| WO | 98/43545 | 10/1998 |
| WO | 99/12480 | 3/1999 |
| WO | WO 99/47050 | 9/1999 |
| WO | WO 00/12013 | 3/2000 |
| WO | WO 00/51498 | 9/2000 |
| WO | WO 01/78609 | 10/2001 |
| WO | WO 01/95809 A1 | 12/2001 |
| WO | WO 02/43558 A2 | 6/2002 |

OTHER PUBLICATIONS

Office Action issued in parent U.S. Appl. No. 10/151,812 dated Dec. 17, 2004.

Craig D. Morgan, M.D. and S. Ward Casscells, M.D. "Arthoroscopic Meniscus Repair: A Safe Approach to the Posterior Horns", Arthroscopy: The Journal of Arthroscopic of Related Surgery, vol. 2, No. 1, 1986 (10 pages).

Richard C. Gardner, 1975, The Hand, "A Malleable Needle for Tendon Surgery," pp. 185-186.

Loré, John Marion, *Tender Grip Forceps*, American Journal of Surgery, vol. 104, Jul. 1962.

1997 Products Catalog, Smith & Nephew, Inc., Shoulder Arthroscopy, 3 pages, Printed Mar. 1997.

1998 Products Catalog, Endoscopy Division, Smith & Nephew, Inc., Shoulder Arthroscopy, 6 pages, Mar. 1998.

1999 Products Catalog, Endoscopy Division, Smith & Nephew, Inc., Shoulder Arthroscopy, 3 pages, Mar. 1999.

2001 Products Catalog U.S. Market, Endoscopy Division, Smith & Nephew, Inc., Shoulder Arthroscopy, 3 pages, Dec. 2000.

2002 Products Catalog U.S. Market, Endoscopy Division, Smith & Nephew, Inc., Knee Arthroscopy, Shoulder Arthroscopy, 6 pages, Printed Dec. 2001.

Elite and Arthro-Pierce Shoulder Instrument Systems Brochure, 2001, Smith & Nephew, Inc., 4 pages, printed Feb. 2001.

Introducing the Acufex Suture Punch Suturing made simple. 1997, Smith & Nephew, Inc., 1 page.

Esch, James C. M.D., Arthroscopic Rotator Cuff Repair with the Elite Shoulder System, A Smith & Nephew Technique Plus Illustrated Guide, 2001, Smith & Nephew, Inc., 15 pages, Oct. 2001.

Closing the Gap in Soft Tissue Repair, The AutoCuff System, 2003, Opus Medical, Inc., 4 pages.

The Elite Shoulder System Brochure, 1999, OBL, Inc., 4 pages.

Golano, Pau, et al., Arthroscopic Anatomy of Posterior Ankle Ligaments, Arthroscopy: The Journal of Arthroscopic and Related Surgery, vol. 18, No. 4 Apr. 2002: pp. 353-358.

The Easy-to-use ArthroSew Suturing System for passing braided suture fast and effectively, 1997, Surgical Dynamics, 2 pages, May 1997.

Acufex Suture Punch Suturing made simple, 1997, Smith & Nephew, Inc., 2 pages, Feb. 1997.

Field, Larry D., M.D., The Elite Arthroscopic Rotator Cuff Repair Shoulder System, 1999, OBL, Inc., 4 pages.

Arthrex, FASTak and Corkscrew Suture Anchor System for Rotator Cuff Repair, 1996 Smith & Nephew, Inc., 1 page.

Elite and Arthro-Pierce Shoulder Instrument Systems Ordering Information, 2002, Smith & Nephew, Inc., 2 pages, Aug. 2002.

Esch, James, C., M.D., The Elite Arthroscopic Rotator Cuff Repair Shoulder System, 1999, OBL, Inc., 12 pages.

OBL Arthro-Pierce Making it Simple, 2000, OBL, Inc., 2 pages.

Field, Larry D., M.D., The Elite Shoulder System, 1999, OBL, Inc., 4 pages.

OBL, Hospital Price List, Jul. 1, 2000, OBL, Inc., 4 pages.

From our skilled hands to yours. Hand-Held Instrument Guide, 1997, Smith & Nephew, Inc., 13 pages, Aug. 18, 1997.

The Complete System for Shoulder Arthroscopy, Innovative Solutions for Arthorscopists, 2000, T.A.G. Medical Products, 7 pages, Jan. 2001 and Feb. 2000.

Arthrex Transtibial Arthroscopic PCL Reconstruction Surgical Technique Manual, 1999, Arthrex, Inc., 27 pages.

(56) References Cited

OTHER PUBLICATIONS

Arthrex Transtibial Single Incision ACL Reconstruction using Three Autograft Options, 1998, Arthrex, Inc., 32 pages.
Suture Punch, 1993, ArthroTek, Inc., 2 pages.
The ExpressSew, Suture Passer, The 5mm Solution for Tissue Repair, 2002, Surgical Solutions, LLC, 5 pages.
Introducing the Acufex Suture Punch, 1997, Smith & Nephew, Inc., 4 pages, Jan. 1997.
ExpressSew, Suture Passer, Surgical Solutions, 5 pages, Apr. 2003.
Romeo, Anthony A., M.D., Arthroscopic Repair of Full-Thickness Rotator Cuff Tears: Surgical Technique and Instrumentation, Orthopedic Special Edition, vol. 7, No. 1 of 2, 2001, pp. 25-28.

* cited by examiner

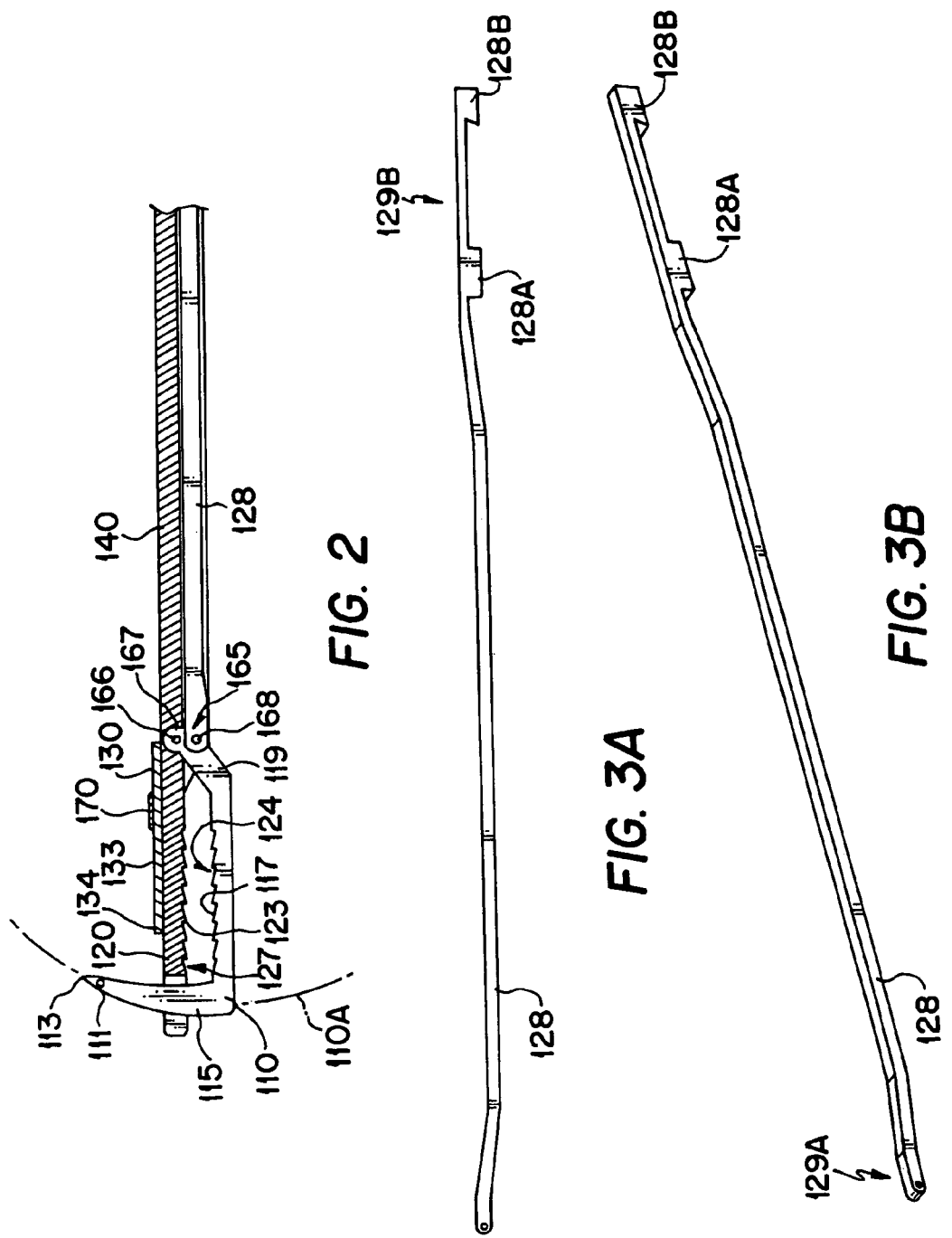

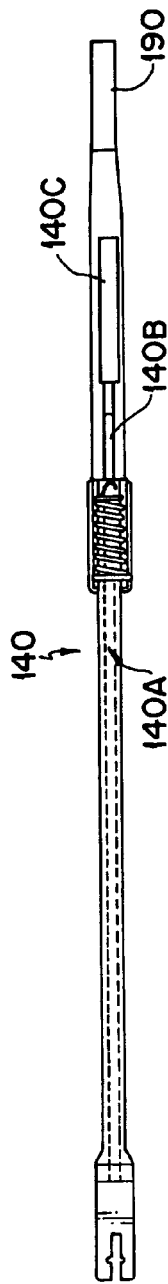
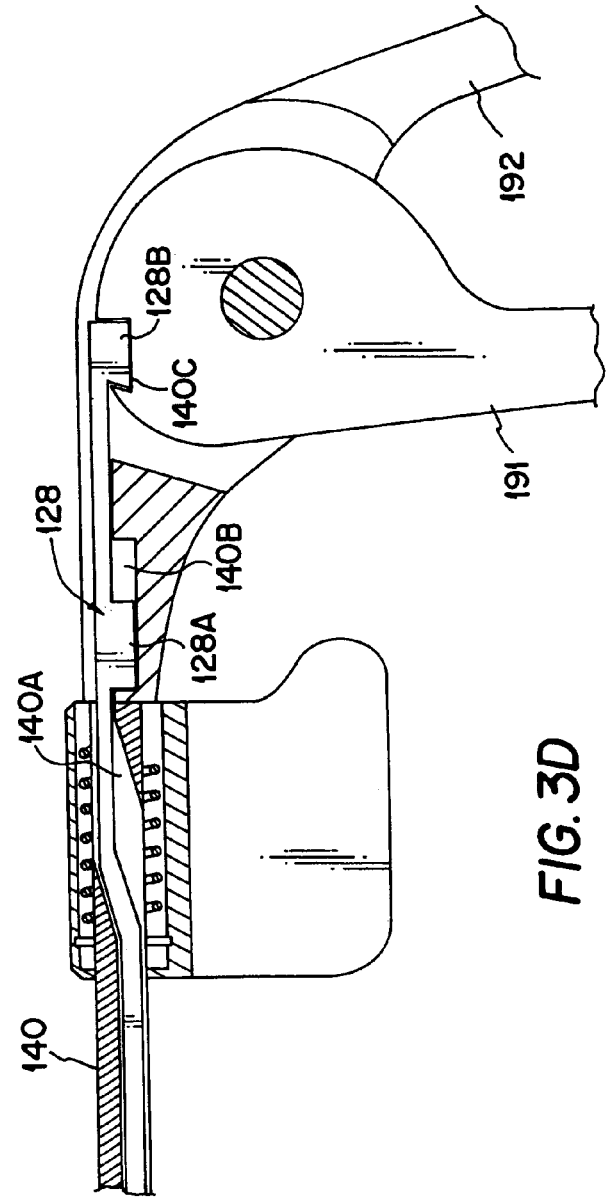
FIG. 3C
FIG. 3D

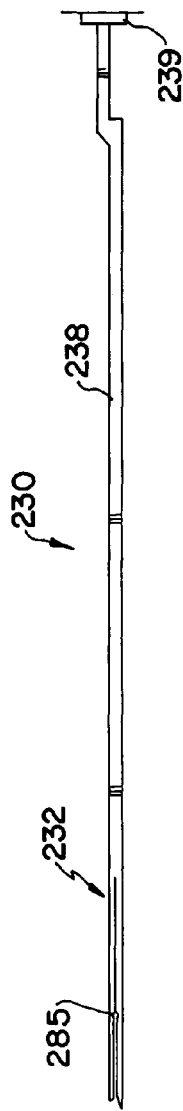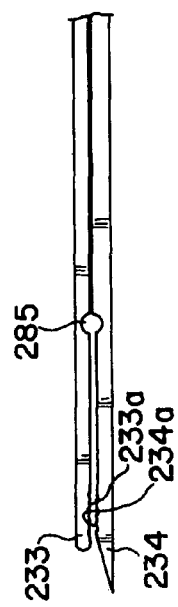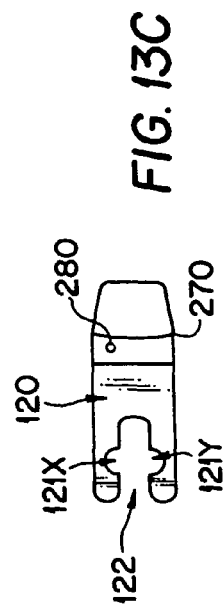
FIG. 13A
FIG. 13B
FIG. 13C

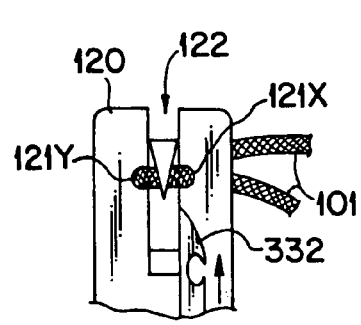
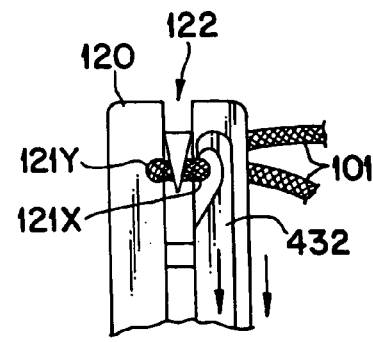
FIG. 14A          FIG. 14B
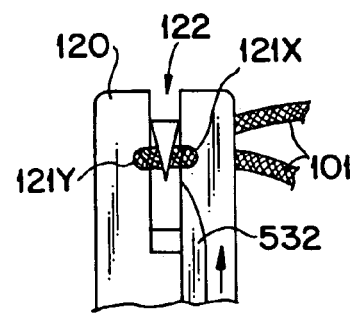
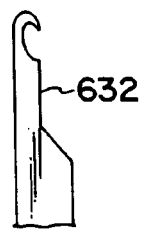
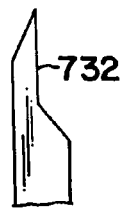
FIG. 14C          FIG. 14D     FIG. 14E
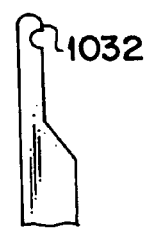
FIG. 14F          FIG. 14G     FIG. 14H

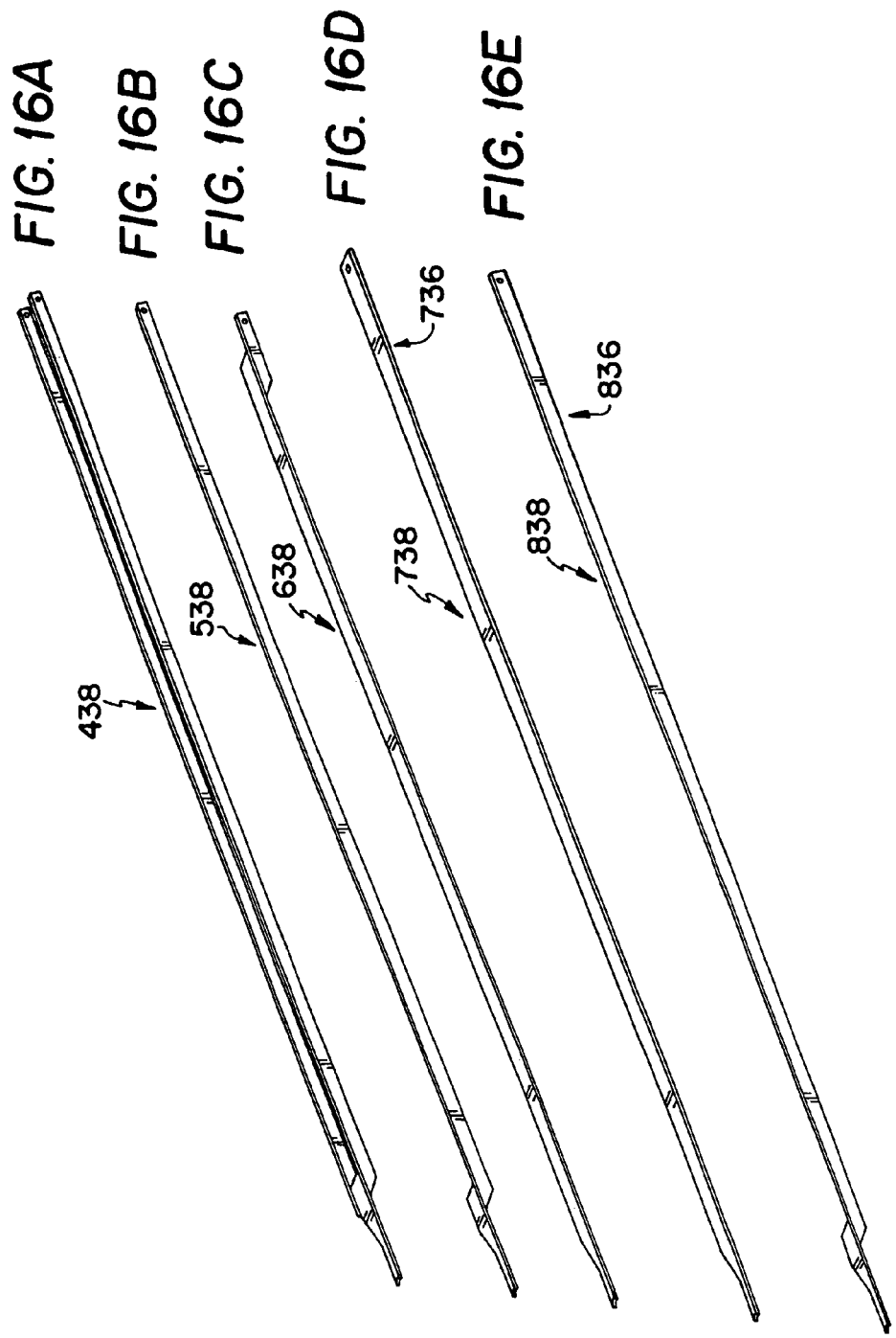

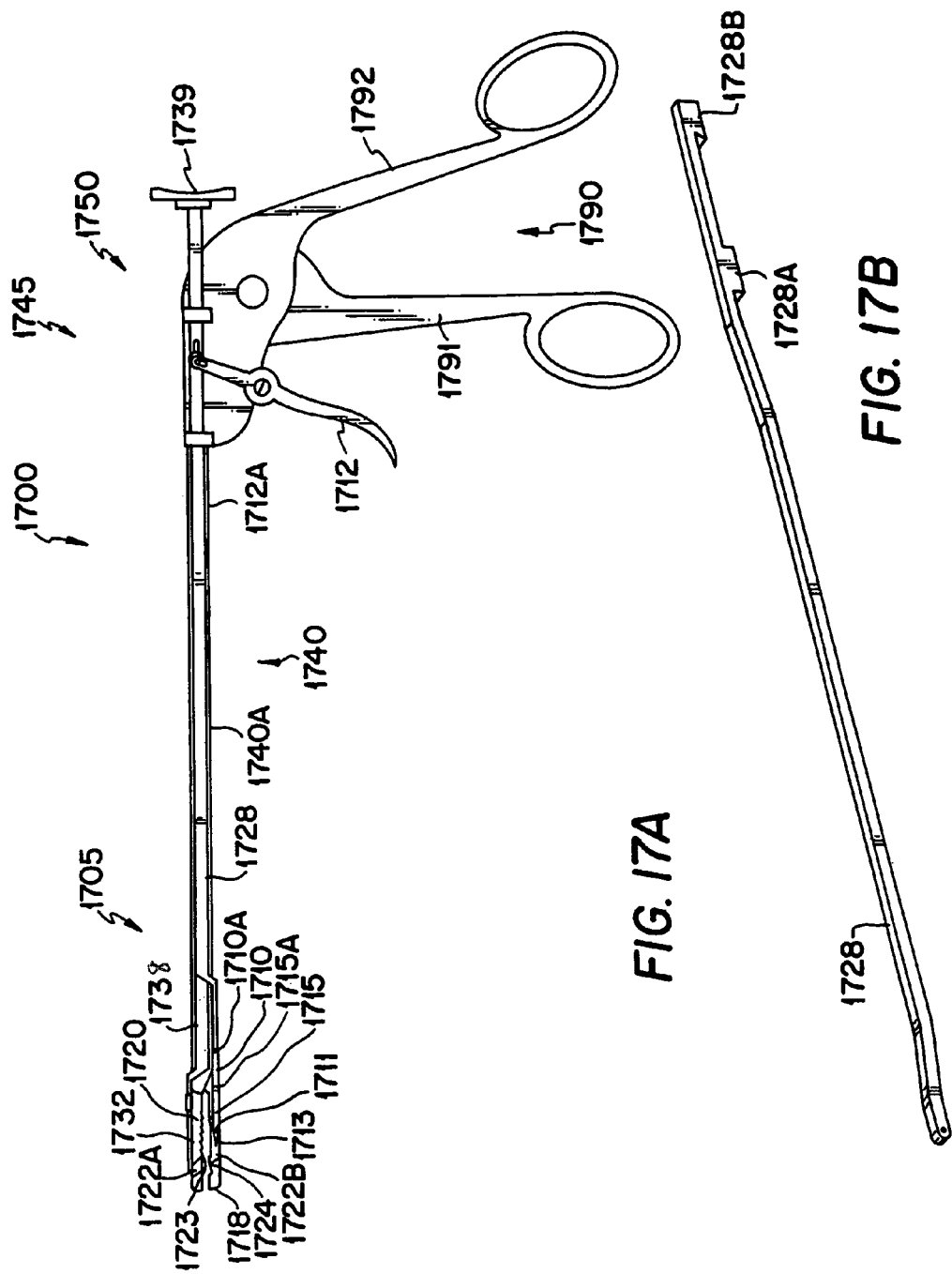

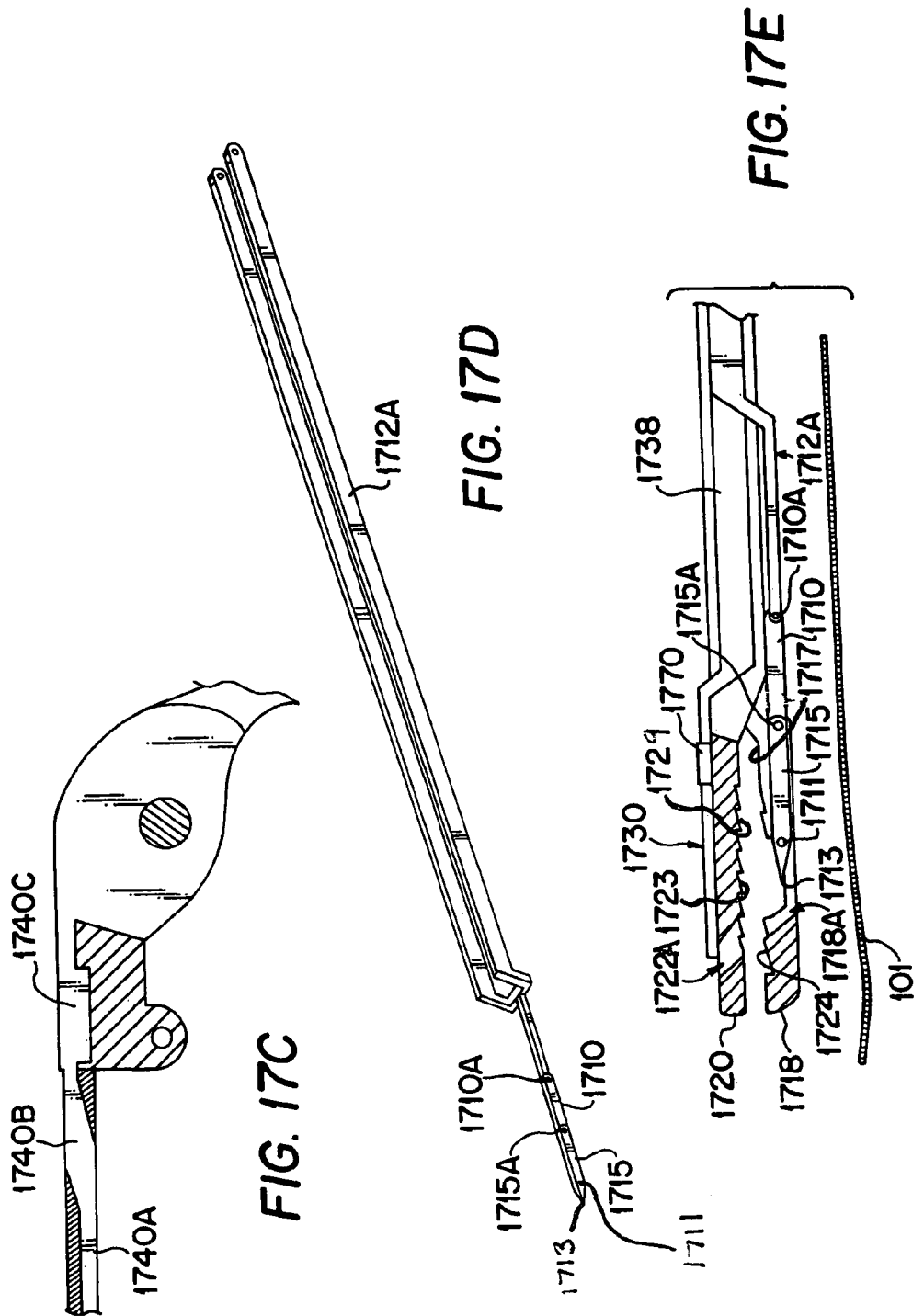

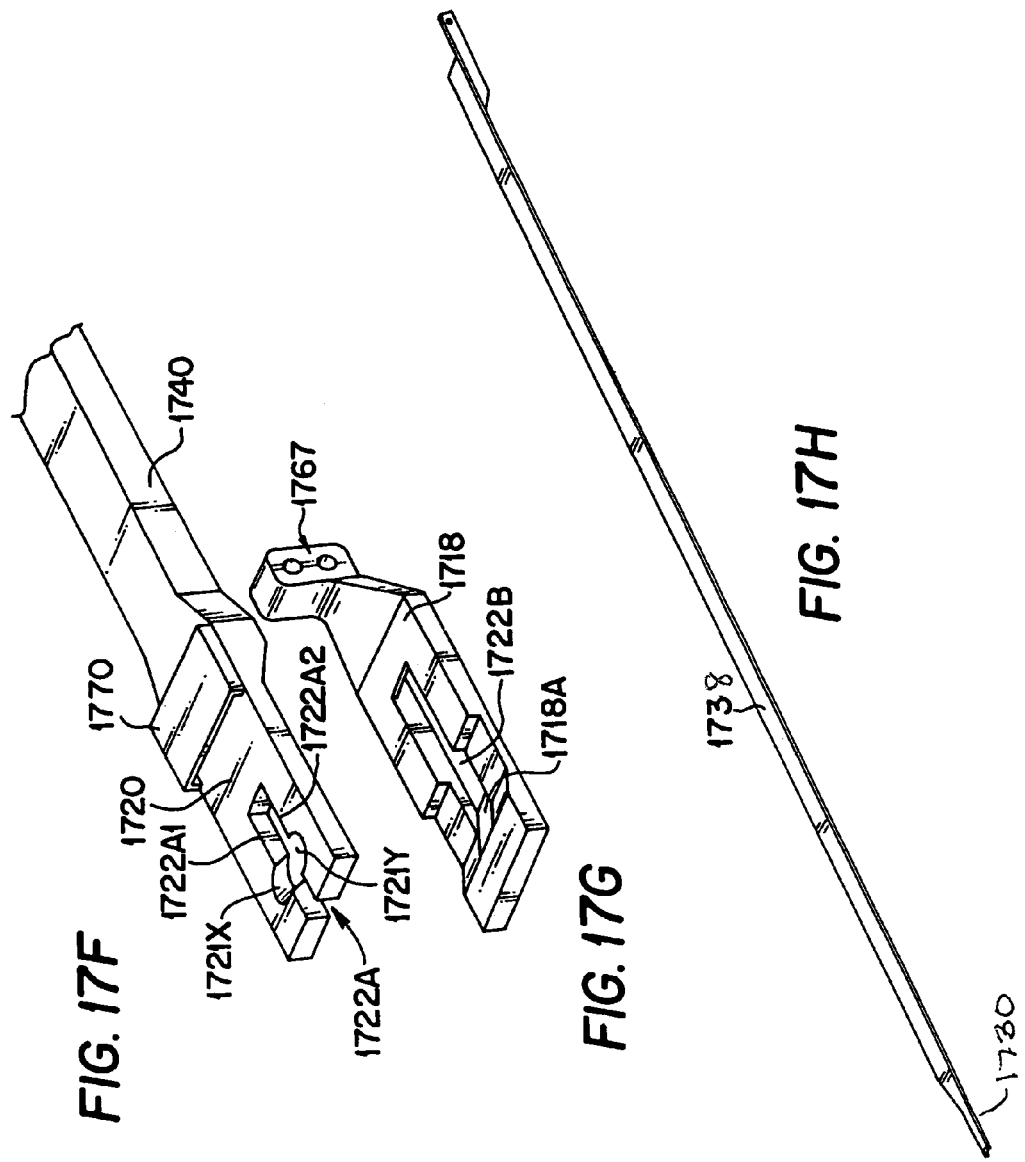

SUTURE PASSING SURGICAL INSTRUMENT

CROSS REFERENCE TO RELATED APPLICATION

This application is a continuation (and claims the benefit of priority under 35 USC 120) of U.S. application Ser. No. 10/151,812, filed May 22, 2002 and issued as U.S. Pat. No. 6,984,237. The disclosure of the prior application is considered part of (and is incorporated by reference in) the disclosure of this application.

TECHNICAL FIELD

This invention relates to suture passing surgical instruments, and more particularly, to a surgical instrument and method for single-handedly passing suture through tissue.

BACKGROUND

Suture is passed through tissue many ways including, for example, cannulated needles and instruments and needle passing instruments, which in general, require the use of multiple portal entry points in order to transfer the suture through tissue or require the use of additional instruments or devices to facilitate the passage of suture. As described in U.S. Pat. No. 5,935,149, it is known to place the suture at a desired site to be sutured by passing a needle attached to the suture from a first member of a suture passing forceps to a second member of the forceps. The suture is secured at the site by passing the needle through a suture receiving passage in an outer member of a suture securing device to position a portion of the suture therein and inserting an inner member of the suture securing device into the passage to secure the portion of the suture between the inner and outer members. The needle is passed through the passage by threading the needle through a suture threader disposed in the passage and pulling the threader from the passage. The suture threader has one end terminating in the needled suture and an opposite end terminating in a suture receiving loop.

SUMMARY

In one general aspect of the invention, a surgical instrument includes first and second members configured to receive tissue therebetween. The first member is adapted to receive suture, the second member is coupled to the first member, and a grasper is coupled to the second member for engaging the suture received by the first member.

Embodiments of this aspect of the invention may include one or more of the following features. The grasper is coupled to the second member for movement between a retracted position and a suture engaging position. The second member defines a slot for receiving suture from the first member, and the grasper is configured to trap suture within the slot. The first member is configured to move relative to the second member between an open position and a closed, tissue piercing position. The second member defines a passageway for receiving a portion of the first member. The second member defines a slot for receiving suture from the first member. The slot opens into the passageway.

The first member includes a needle for piercing tissue. The needle defines an eyelet for receiving suture. The eyelet includes a hole. Alternatively, the eyelet includes two holes. In another alternative, the eyelet includes a cutout.

The surgical instrument also includes a handle that controls movement of the first member. The handle includes an articulating handle and a stationary handle.

The second member includes a passageway that receives a portion of the first member. The second member includes at least one suture slot that is disposed in a lengthwise side of the passageway. Also, the at least one suture slot opens to the passageway.

The first member includes a jaw and a needle arm extending from a distal end of the surgical instrument. The needle arm is adapted to receive suture. The jaw defines a passageway that receives a portion of the needle arm. The second member defines a passageway that receives a second portion of the needle arm. The second member defines at least one suture slot that is disposed in a lengthwise side of the passageway and opens to the passageway. The suture grasper engages the suture and holds the suture in the at least one suture slot.

The grasper is disposed on a portion of the second member. The grasper includes a hook. Alternatively, the grasper includes a wedge. In another alternative, the grasper includes a set of jaws. In another alternative, the grasper includes a U-shaped cup.

The surgical instrument includes a trigger that controls the grasper. The trigger is a paddle. Alternatively, the trigger is a lever. In another alternative, the trigger is a button. The surgical instrument also includes a grasper guide that is disposed on a portion of the second member. The trigger moves the grasper distally under the grasper guide to engage the suture.

A portion of the first member is serrated. A portion of the second member is serrated.

In another general aspect of the invention, a method of passing suture includes loading suture into a first member of a suture passing surgical instrument, stabilizing tissue between the first member and a second member of the surgical instrument, passing suture through tissue via the first member of the surgical instrument, holding the passed suture via a suture grasper of the surgical instrument, and removing the first member from the tissue.

Embodiments of this aspect of the invention may include one or more of the following features. After loading suture, the surgical instrument is passed through a cannula. The method also includes removing the surgical instrument from the surgical site.

Loading suture includes loading suture from a side of the surgical instrument. Loading suture further includes loading suture from the side of the surgical instrument on which the suture grasper is located.

The method includes stabilizing tissue and passing suture through tissue simultaneously.

The method includes passing suture multiple times. Passing suture multiple times includes loading suture into the first member of the suture passing surgical instrument, and passing suture through tissue via the first member of the suture passing instrument.

Conventional instruments and methods for passing suture generally require multiple portal entry points and/or supplemental instruments to facilitate passage of suture. The surgical instrument of this invention overcomes these difficulties. In particular, the instrument and method provide a surgeon with the ability to single-handedly pass suture through tissue. As a result, only one portal and one instrument are required.

The details of one or more implementations are set forth in the accompanying drawings and the description below. Other

DESCRIPTION OF DRAWINGS

FIG. 2 is a partial cross-sectional view of a distal portion of the surgical instrument of FIG. 1 in which an articulating jaw is closed.

FIG. 3A is a side view and FIG. 3B is a perspective view of a push/pull rod for the articulating jaw of the surgical instrument of FIG. 1.

FIG. 3C is a top view of an elongated shaft of the surgical instrument of FIG. 1.

FIG. 3D is a partial cross-sectional view of a proximal portion of the surgical instrument of FIG. 1.

FIG. 13A is a side view of an alternate implementation of the suture grasper.

FIG. 13B is a detailed view of the suture capture device of the suture grasper of FIG. 13A.

FIG. 13C is a top view of an alternate implementation of the tissue platform provided with the suture grasper of FIG. 13A.

FIGS. 14A-14H are top views of alternative implementations of the suture capture device of the suture grasper.

FIGS. 16A-16E are top views of alternative implementations of push/pull rods of the suture grasper.

FIG. 17A is a side view of an alternate implementation of the suture passing surgical instrument.

FIG. 17B is a perspective view of the push-pull rod of the cross-sectional view of a proximal portion of the surgical instrument of FIG. 17A.

FIG. 17C is a detailed cross-sectional view of a proximal portion of the surgical instrument of FIG. 17A.

FIG. 17D is a perspective view of a needle arm of the surgical instrument of FIG. 17A.

FIG. 17E is a partial cross-sectional view of a distal portion of the surgical instrument of FIG. 17A.

FIG. 17F is a perspective view of a first jaw of the surgical instrument of FIG. 17A.

FIG. 17G is a perspective view of a second jaw of the surgical instrument of FIG. 17A.

FIG. 17H is a view of the suture grasper push rod that can be used in the surgical instrument of FIG. 17A.

Like reference symbols in the various drawings indicate like elements.

DETAILED DESCRIPTION

Figure 1:
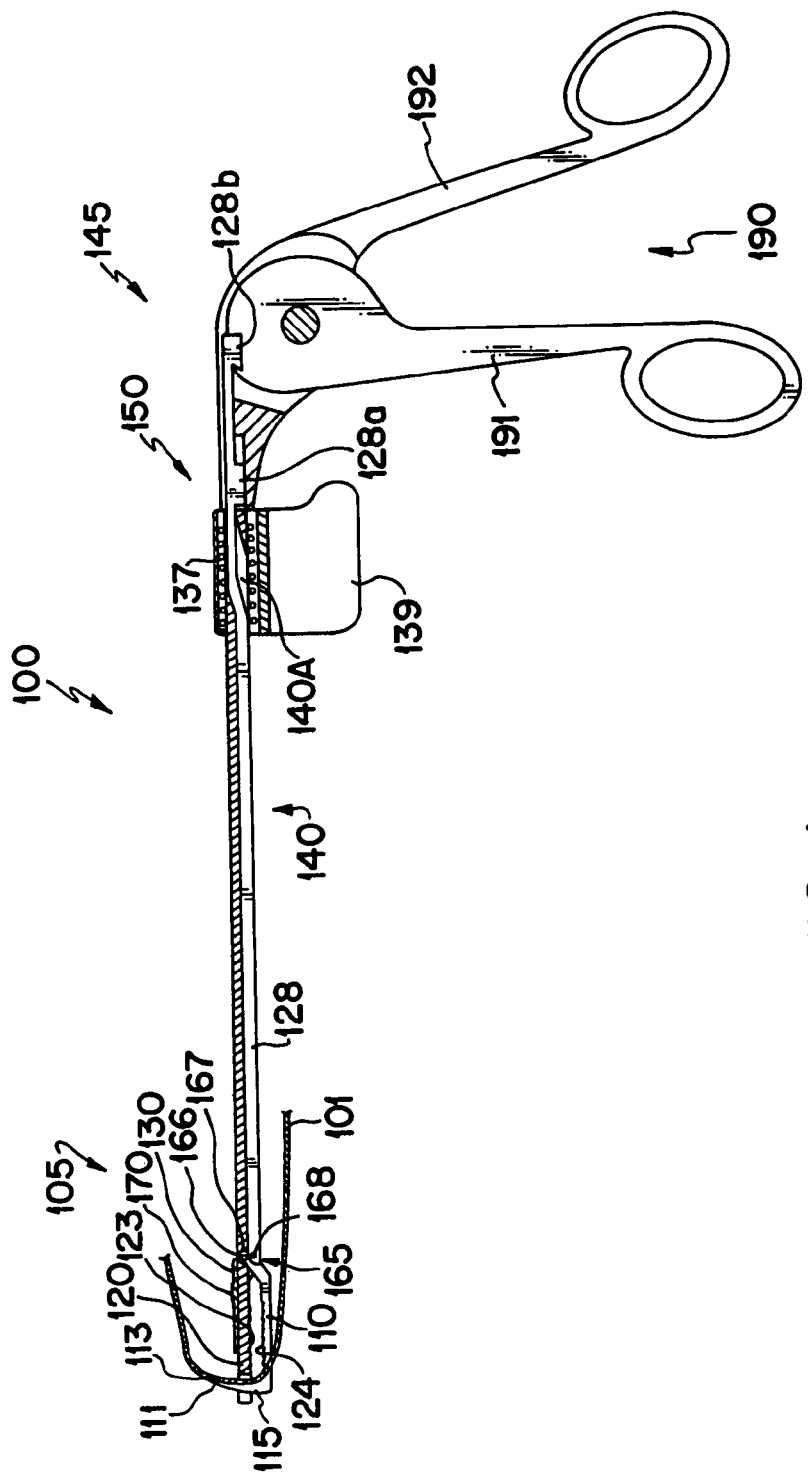
FIG. 1 is a partial cross-sectional view of an exemplary suture passing surgical instrument.

Referring to FIG. 1, a single-handed suture passing surgical instrument 100 passes suture 101 through tissue and holds the passed suture such that the instrument can be rethreaded to pass suture through tissue multiple times. An operator actuates a handle 190 to close an articulating jaw 110 through which suture is threaded to pass the suture through tissue, and thereafter actuates a trigger portion 150 to advance a suture grasper 130 along a tissue platform 120 to engage the suture with the suture grasper 130. The jaw 110 is then opened and the instrument 100 removed with the suture remaining in the tissue and held by the suture grasper 130. The instrument 100 can be rethreaded and reinserted to the surgical site to pass suture multiple times, for instance, as with a Mason-Allen Stitch.

Suture passing surgical instrument 100 includes an elongated shaft 140 with a distal portion 105 and a proximal portion 145. Located at the proximal portion 145 of the elongated shaft 140 are handle 190 and trigger portion 150. Located at the distal end 105 are articulating jaw 110, tissue platform 120, and suture grasper 130.

The articulating jaw 110 is pivotally attached to the tissue platform 120, and movement of the articulating jaw 110 is controlled by the handle 190. In use, distal portion 105 is positioned such that when jaw 110 is closed, tissue is held between an upper surface of the articulating jaw 110 and a lower surface of the tissue platform 120. The handle 190 includes an articulating handle 191 and a stationary handle 192. As the articulating handle 191 is moved away from and towards the stationary handle 192, the articulating jaw 110 is opened and then closed, respectively. The articulating handle 191 is attached to a push/pull rod 128, which moves along a groove 140A in the elongated shaft 140. The rod 128 is attached to the articulating jaw 110 by a pivot hinge assembly 165, described further below.

Figure 5A:
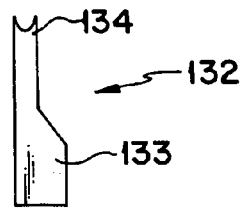
FIG. 5A is an exemplary tip of a suture capture device of the suture grasper and FIG. 5B is an exemplary arm of the suture capture device of the suture grasper of the surgical instrument of FIG. 1.
Figure 5B:
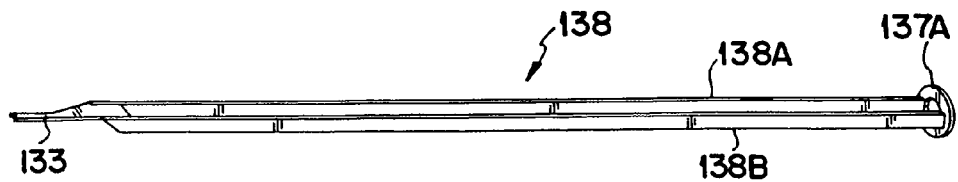

The suture grasper 130 is controlled by the trigger portion 150 and is located on the tissue platform 120. Tissue platform 120 is the distal portion of shaft 140. Generally, the suture grasper 130 is designed to advance forward and hold the suture. The trigger portion 150 includes a trigger mechanism 139 and a rod 138 (see FIG. 5B). The trigger mechanism 139 is attached to the rod 138, which runs along the elongated shaft 140, to control movement of the suture grasper 130.

Referring to FIG. 2, the articulating jaw 110 is attached at its proximal end 119 to the tissue platform 120 by the pivot hinge assembly 165. The pivot hinge assembly 165 includes two pins 166, 168 and a hinge connector 167. The hinge connector 167 is part of the jaw 110 and is attached to the tissue platform 120 by the pin 166 such that the articulating jaw 110 pivots about the pin 166 as the jaw 110 articulates. The rod 128 is attached to the hinge connector 167 by the pin 168 such that forward and backward motion of the rod 128 causes the jaw 110 to pivot about the pin 166.

Referring to FIGS. 3A-3D, the push/pull rod 128 includes two tabs 128A, 128B at its proximal end 129B. Rod 128 is an elongated square-shaped shaft. At its distal end 129A, rod 128 slopes away from its axis. Rod 128 includes this slope in order to articulate the jaw 110 in relation to the action of the handle 190.

The rod 128 reciprocates within groove 140A in the instrument shaft 140 as the articulating handle 191 is moved away from and then towards the stationary handle 192 to open and close the articulating jaw 110. The instrument shaft 140 also includes a limiting groove 140B in which tab 128A is located. The axial movement of tab 128A in limiting groove 140B limits movement of the rod 128 in the axial direction because axial movement of tab 128A within the groove 140B is constrained by the proximal and distal sides of groove 140B. The articulating handle 191 defines a handle slot 140C in which tab 128B is located providing coupling between the rod 128 and the articulating handle 191 such that as the handle 191 is moved, the rod 128 moves to actuate jaw 110.

Referring again to FIG. 2, the articulating jaw 110 includes a needle 115. Generally, the needle 115 is sickle-shaped with a sharp point 113 and is formed of hardened stainless steel or similar material. The needle 115 is formed integral to the articulating jaw 110 and extends from the articulating jaw 110 toward the tissue platform 120. Needle 115 includes a suture eyelet 111 disposed proximate to the tip 113 of the needle 115. The needle 115 is sized such that when the articulating jaw 110 is closed, the instrument can fit within a predetermined sized cannula. Thus, the length of the needle 115 varies with different sized cannulas.

Figure 4A:
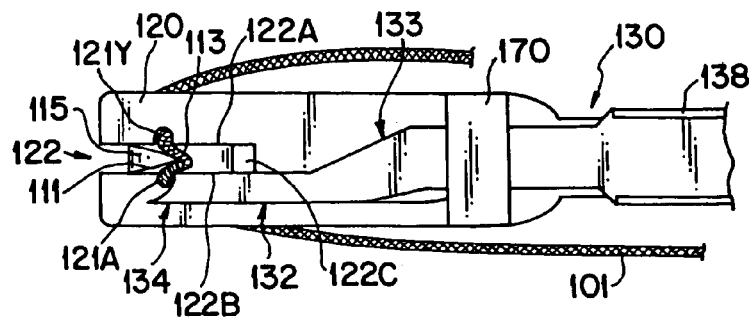
FIG. 4A is a top view of a distal portion of the surgical instrument of FIG. 1 showing a suture grasper capturing the suture and FIG. 4B is a perspective view of the distal portion of the surgical instrument of FIG. 1 showing the eyelet of the needle in line with the suture slots of the passageway.
Figure 4B:
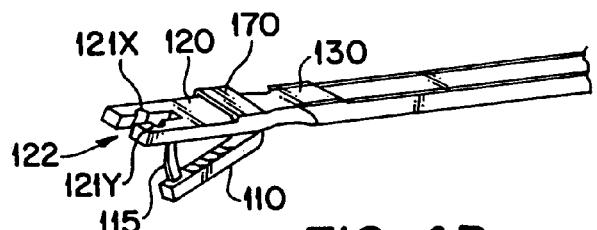

Referring to FIGS. 4A and 4B, the tissue platform 120 has an U-shaped end 122C defining a passageway 122. The passageway 122 includes two suture slots 121X, 121Y. The suture slots 121X, 121Y are positioned such that when the needle passes through passageway 122, the needle eyelet 111 is aligned with the slots when the portion of the needle defining the eyelet is within the passageway 122 to consistently place the suture 101 that is threaded through the eyelet in the suture slots 121X, 121Y (see FIG. 4B). The suture rests in one of the suture slots 121X, 121Y after the needle 115 has passed through the tissue. The slots 121X, 121Y are provided in each of the lengthwise sides 122A, 122B of the passageway 122. Suture grasper 130 acts to move the suture away from the needle 115 and holds the suture, for example, in slot 121X against surface 121A. Additionally, as the suture grasper 130 holds the suture against the wall 121a of the suture slot 121, the suture grasper 130 also closes the opening in side 122A to capture the suture in the suture slot 121X, as explained in more detail below.

Referring to FIGS. 1, 2, 5A, and 5B, the suture grasper 130 is located on the tissue platform 120 and is attached to rod 138. The suture grasper 130 includes a suture capture device 132 in the form of an arm 133 with an U-shaped tip 134. The suture grasper 130 is shown to one side of the passageway 122 (the left side as viewed in FIG. 4A). However, the suture grasper 130 can be located on either side, e.g., right or left, of the passageway 122. To minimize possible damage to the suture, the suture is threaded through the eyelet 111 from the same side on which the suture grasper 130 is located. Rod 138 is formed as a pair of parallel rods 138A, 138B that terminate at their proximal end at a spring plate 137A.

The suture grasper 130 is activated by the trigger portion 150 to capture and hold the suture. The arm 133 of the suture capture device 132 of the suture grasper 130 advances forward to hold the suture in the U-shaped tip 134 against the distal wall 121A of suture slot 121X (FIG. 4A). The tissue platform 120 includes a grasper guide 170 under which the suture grasper 130 moves. The grasper guide 170, for example, is formed like a bridge such that as the suture grasper 130 moves forward to hold the suture in suture slot 121X, the suture grasper 130 follows a direct path towards the distal end 105 of the instrument 100.

The tip 113 of the needle 115 on the articulating jaw 110 passes through the passageway 122 when the articulating jaw 110 is closed. The passageway 122 is slightly wider than the needle 115. The needle 115 pivots about pin 166 along an arc 110a (see FIG. 2). The needle 115 is shaped with an arch, which corresponds to the radius of the arc 110a. Thus, when the needle 115 extends through the passageway 122, it arches over the suture grasper 130. The arch of the needle 115 limits possible tearing of the tissue as the needle passes through the tissue.

Figure 6A:
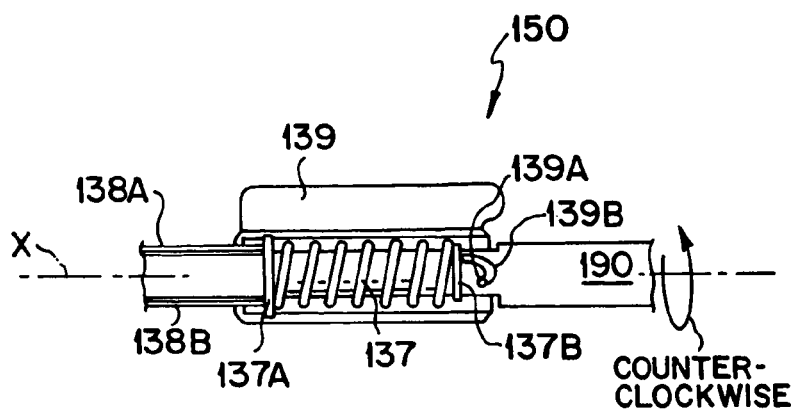
FIG. 6A is a partial cutaway top view of a trigger portion for the suture grasper shown in an open position and FIG. 6B is a partial cutaway top view of the trigger portion for the suture grasper shown in a closed position.
Figure 6B:
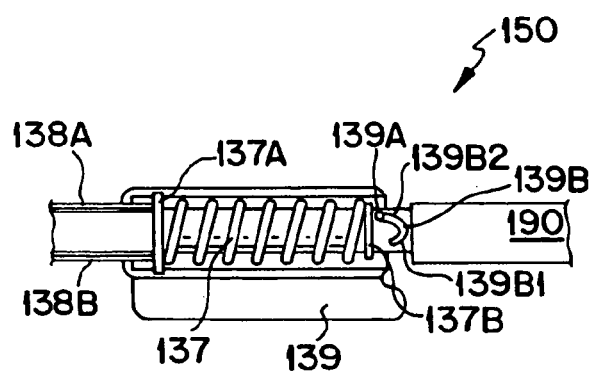

Referring to FIGS. 6A and 6B, the trigger portion 150 for moving the suture grasper 130 includes the trigger mechanism 139, for example, shaped like a paddle, and the push/pull rod 138. The trigger mechanism 139 rotates about an axis X. The trigger mechanism 139 is attached to the push/pull rod 138 that ends in the U-shaped suture capture device 132. The trigger portion 150 also includes a rigid pin 139A that follows a J-shaped groove 139B in the trigger mechanism 139 and a spring 137.

In its resting position, the suture grasper 130 is in an open, locked position with pin 139A located in the hook side 139B1 of the J-shaped groove 139B, as shown in FIG. 6A. To create the forward movement of the suture grasper 130 necessary to capture the suture, the trigger mechanism 139 is rotated counter-clockwise (looking from the proximal end 190 down the shaft 140) to move the pin 139A from the hook side 139B1 of the J-shaped groove 139B to the long side 139B2 of the J-groove 139B, as shown in FIG. 6B. The movement of the pin 139A within the groove 139B forces the push/pull rod 138 forward and the trigger mechanism 139 proximally and then distally against the spring 137. The forward movement of the suture grasper 130 is created as the spring 137 moves forward against a spring plate 137A and back against a spring brake or spring plate 137B. To return the suture grasper 130 to its resting position, the trigger mechanism 139A is rotated clockwise, e.g., moved from the long side 139B2 of the J-shaped groove 139B back to the hook side 139B1 of the J-shaped groove 139B.

Figure 7A:
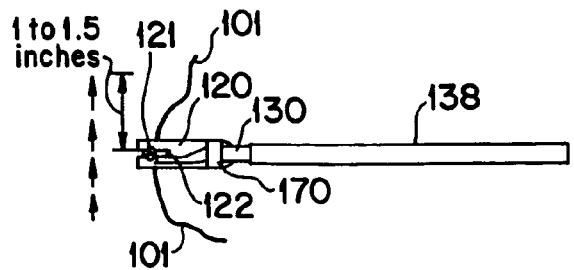
FIGS. 7A-7O illustrates use of the surgical instrument of FIG. 1.
Figure 7B:
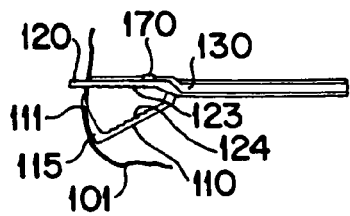
Figure 7C:
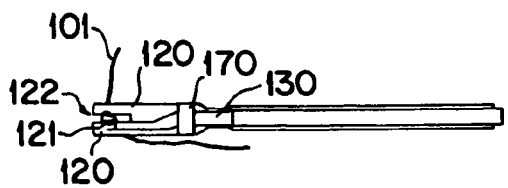

Referring to FIGS. 7A-7K, an operator uses the suture passing surgical instrument as follows. As shown in FIGS. 7A (top view) and 7B (side view), an operator opens the articulating jaw 110, i.e., articulating the jaw 110 away from tissue platform 120, by moving handle 190 and loads suture into the suture eyelet 111 of the needle 15. As shown in FIG. 7C (top view), the operator moves handle 190 to close articulating jaw 110 to hold the suture in the eyelet 111.

Figure 7D:
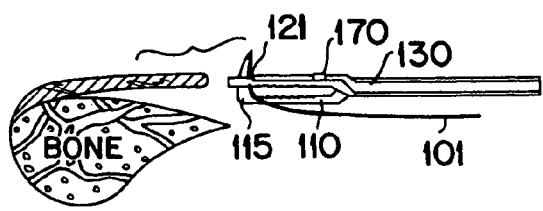
Figure 7E:
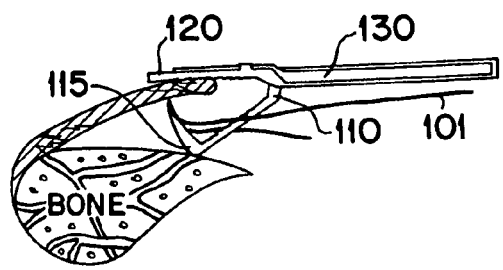
Figure 7F:
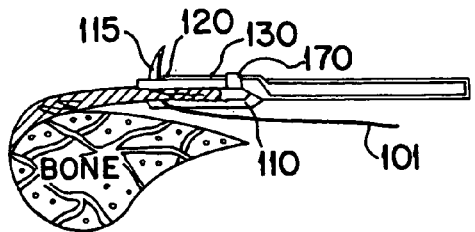
Figure 7G:
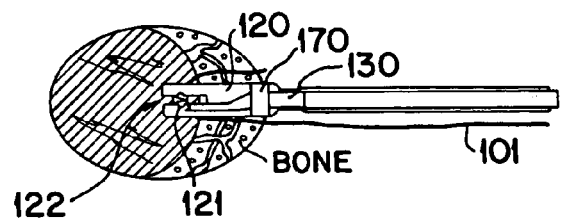

Then, as shown in FIG. 7D (side view), the operator passes the instrument 100 down a cannula to the surgical site. As seen in FIG. 7E (side view), after placing the instrument 100 in the surgical site, the operator moves handle 190 to open articulating jaw 110 to place the needle 115 under the targeted tissue. As shown in FIGS. 7F (side view) and 7G (top view), the operator moves handle 190 to close articulated jaw 110 to capture the targeted tissue between the jaw 110 and the tissue platform 120. The needle 115 on the articulating jaw 110 pierces the tissue as the tissue is grasped between the tissue platform 120 and the articulating jaw 110, carrying the suture through the tissue.

Figure 7H:
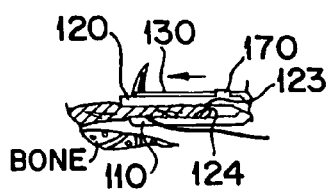
Figure 7I:
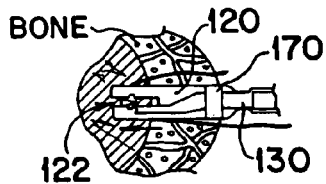
Figure 7J:
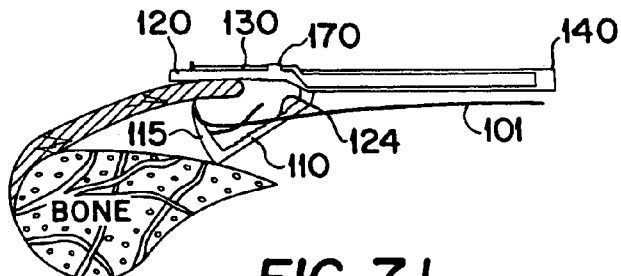
Figure 7K:
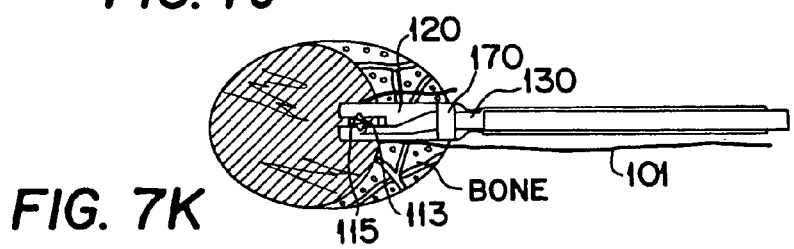

Next, as shown in FIGS. 7H (side view) and 7I (top view), the operator moves trigger portion 150 to advance suture grasper 130 forward to hold suture in the suture slot 121Y. As shown in FIGS. 7J (side view) and 7K (top view), the suture passed through the tissue is trapped on the proximal side of the tissue.

Figure 7L:
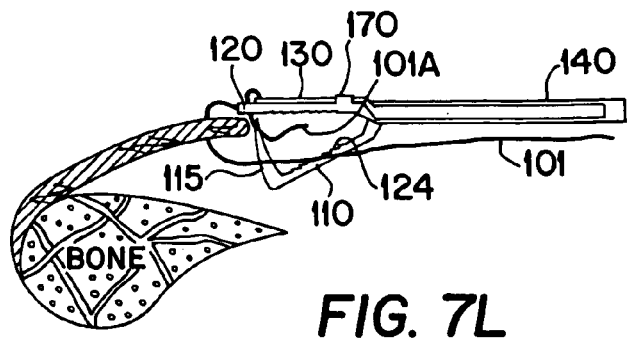
Figure 7M:
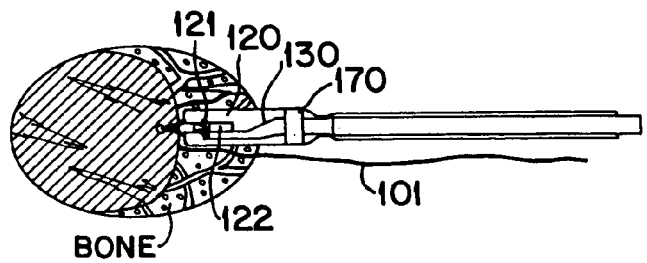
Figure 7N:
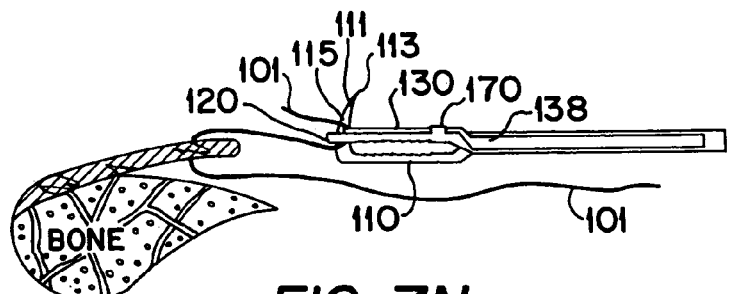
Figure 7O:
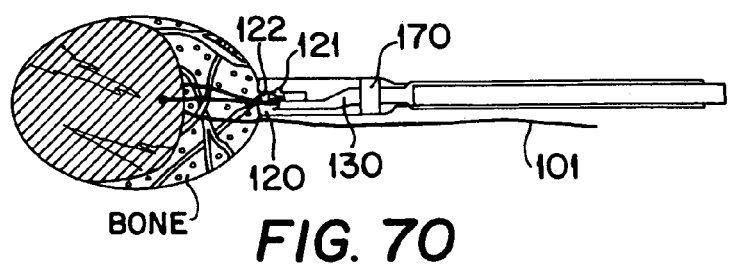

As shown in FIGS. 7L (side view) and 7M (top view), the operator moves handle 190 to open articulating jaw 110 to release the tissue. As the jaw 110 is opened, the suture grasper 130 holds the suture against wall 121A of suture slot 121X. As the operator begins to withdraw the instrument 100 from the surgical site, the free end of the suture slides out of eyelet 111 of needle 115. As shown in FIGS. 7N (side view) and 7O (top view), the free end 101A of the suture 101 (the end that was threaded through the eyelet 111) remains above the tissue platform 120. The other end of the suture is located in suture slot 121X and passes through the tissue. The operator moves handle 190 to close jaw 110 to withdraw instrument 100 through the cannula (not shown). The instrument may be rethreaded and reinserted through the cannula to the surgical site in order to pass suture multiple times. For instance, where most tendon tissue are fibrous bundles, a repair that can be less prone to tearing along the fibrous bundle structure can be possible when the suture is secured perpendicular to the bundle cord with multiple passes of the suture. By passing suture through a different tissue bundle, the suture/tendon interface can be improved.

Figure 8A:
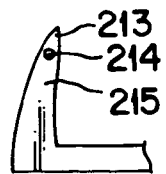
FIGS. 8A-8H illustrate alternative configurations of a suture eyelet of a needle of the surgical instrument of FIG. 1.
Figure 8B:
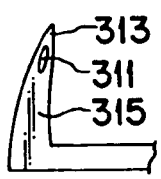
Figure 8C:
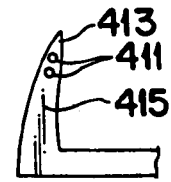
Figure 8D:
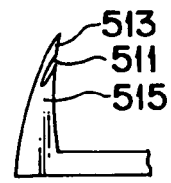
Figure 8E:
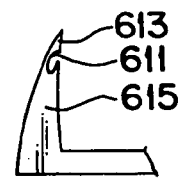
Figure 8F:
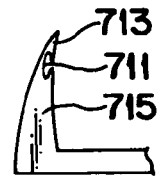
Figure 8G:
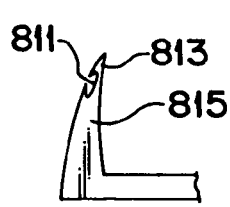
Figure 8H:
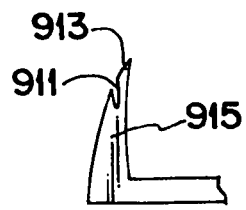

Numerous alternative implementations or configurations of elements of the surgical instrument are possible. For instance, referring to FIGS. 8A-8H, the suture eyelet disposed proximate to the tip of the needle can have a variety of shapes and/or orientations. For example, FIG. 8A shows a rounded hole 211 as the suture eyelet, whereas FIG. 8B shows an oval or oblong hole 311 as the suture eyelet. In an alternative implementation, there can be more than one hole 411, as shown in FIG. 8C. Or, the suture eyelet can be a cutout in the side of the needle proximate to the tip. For example, FIGS. 8D and 8E show cutouts 511, 611 that extend into the needle, toward the jaw 110. Alternatively, FIG. 8F shows a cutout 711 disposed below the tip 713 of the needle 715 that extends in both toward the tip 713 and toward the jaw 110. Or, the eyelet can be located on the rounded side of the needle, as shown in FIGS. 8G and 8H (e.g., cutouts 811, 911).

The various positions and shapes of the suture eyelets affect a surgeon's ability to load/unload suture, to penetrate tissue, and to minimize procedure length. For instance, the suture may be threaded through the rounded hole or closed eyelet type of suture eyelets, as shown, for example, in FIG. 9. While loading suture requires a bit more skill, the closed eyelet type of suture needle penetrates tissue more easily and accurately. Additionally, for example, the double eyelet needle shown in FIG. 8C may be used to pass two sutures simultaneously to form a mattress stitch with one pass and hence, reduce surgical time. With the cutout-type of suture eyelet, the suture is easier to load/unload, but tissue is more difficult to penetrate. Regardless of type or orientation of suture eyelet, suture is loaded on the same side that the suture grasper is located.

Figure 9:
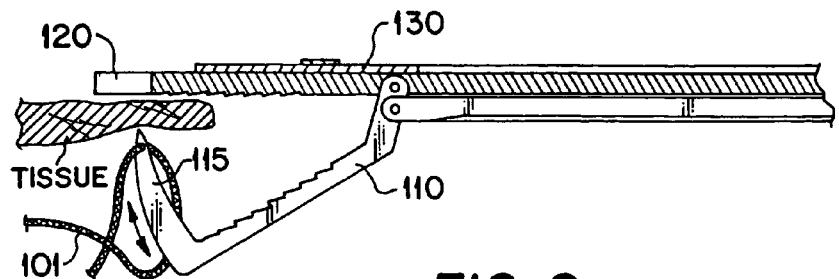
FIG. 9 shows a suture threaded through the suture eyelet of the needle of the surgical instrument of FIG. 1.
Figure 10:
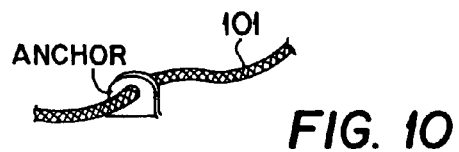
FIG. 10 shows a suture attached to an exemplary soft tissue attachment device.

The various embodiments discussed can include "free" suture or suture attached to a soft tissue attachment device. As shown in FIG. 9, the "free" suture (suture not attached to an external device) is threaded through the suture eyelet 111 of the needle 115. The ability to use "free" suture with the suture passing surgical instrument provides a surgeon with the flexibility to use intricate weaving (suture) patterns without the demand of visualizing each suture transfer. Alternatively, referring to FIG. 10, suture is attached to a soft tissue attachment device, e.g., an anchor, prior to being threaded through the suture eyelet 111.

Figure 11:
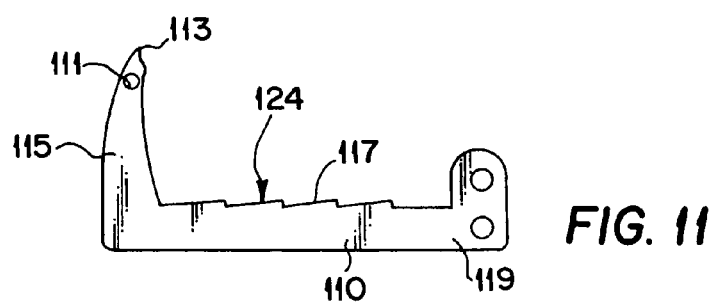
FIG. 11 is a detailed side view of an articulating jaw of the surgical instrument of FIG. 1 showing serrations.

Referring to FIG. 11, the surface 117 of the horizontal portion of the articulating jaw 110 (the surface facing the tissue platform 120) includes serrations 124 (see also FIG. 2). The serrations 124, for example, are "V" shaped and provide an increased surface area against which to hold the tissue. The shape, number, and length of the serrations 124 can, for instance, vary. The serrations 124 can be, for example, grooves, ribs, or ridges. Alternatively, the surface 117 is smooth, i.e., without serrations, as shown in FIGS. 8A-8H.

Figure 12:
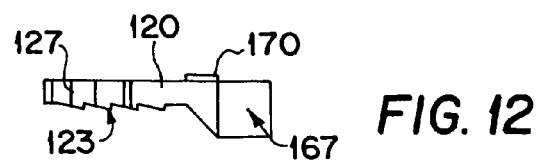
FIG. 12 is a detailed side view of a tissue platform of the surgical instrument of FIG. 1 showing serrations.

Referring to FIG. 12, the surface 127 of the tissue platform 120 (the surface that faces the articulating jaw 110) includes serrations 123 (see also FIG. 2). The serrations 123 of the tissue platform 120 are, for instance, V-shaped and provide a larger surface against which to hold the tissue after the needle 115 has penetrated the tissue. The shape, number and length of the serrations 123 can vary. For example, the serrations 123 can be grooves, ribs, or ridges. A surgeon may want to move the tissue after it has been grabbed to ensure that the tissue will reach the attachment site. Or, if the detached tissue creates adhesions to other tissue surfaces, by pulling on the held tissue, the surgeon can determine if it is necessary to release or cut those adhesions free.

Referring to FIGS. 13A-13C, an alternative implementation of the suture grasper 230 includes a suture capture device 232 having two opposing jaws 233, 234 that, when advanced forward, flex outward to open around the suture and then spring shut to enclose the suture between the two jaws 233, 234. The suture grasper 230 is moved forward by activation of a push-pull rod 238 by an alternative implementation of the trigger mechanism 339, a thumb push plate. The opposing jaws 233, 234 of the suture grasper 230 initially contact an expansion pin 280, which causes the jaws 233, 234 to open. The jaws 233, 234 of the suture capture device 232 include a plurality of grasping teeth 233*a*, 234*a* on their facing surfaces for holding the suture. The suture grasper 230 continues to move forward until the expansion pin 280 enters the expansion pin release slot 285, at which point the opposing jaws 233, 234 of the grasper 230 close on the suture.

A grasper guide 270 provides directional guidance for the suture grasper 230 as the grasper moves forward along shaft 140 to capture the suture from the needle (not shown). The grasper guide 270 is a raised structure, e.g., a bridge, under which the suture grasper 230 moves. In this implementation of the guide 270, the expansion pin 280 is located between the grasper guide 270 and the tissue platform 120.

Other implementations or configurations of a suture capture device include, for example, a hook or pick that advances forward or moves backward, pushes the suture away from the needle, and captures the suture. For example, the hook may be a forward-moving hook 332, as shown in FIG. 14A; a backward-moving hook 432, 632, as shown in FIGS. 14B and 14D; a forward-moving wedge 532, 732, as shown in FIGS. 14C and 14E; or a forward- or backward-moving hook 1032, as shown in FIG. 14H. Alternatively, as shown in FIGS. 14F and 14G, the cup-shape of the suture capture device can have sides of different lengths (FIG. 14F) 832 or a flat base of the cup (FIG. 14G) 932. As illustrated, for example, in FIGS. 14D-14H, the suture capture device alternatives are shown located on the left side of the tissue platform. However, the suture capture device can be located on the right side of the tissue platform, for example, as in FIGS. 14A-14C, if the suture were loaded from a different direction.

Figure 15A:
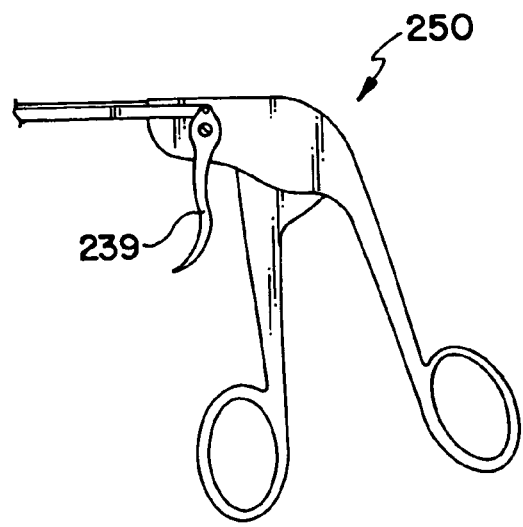
FIG. 15A is a side view of the alternative implementation of the trigger.
Figure 15B:
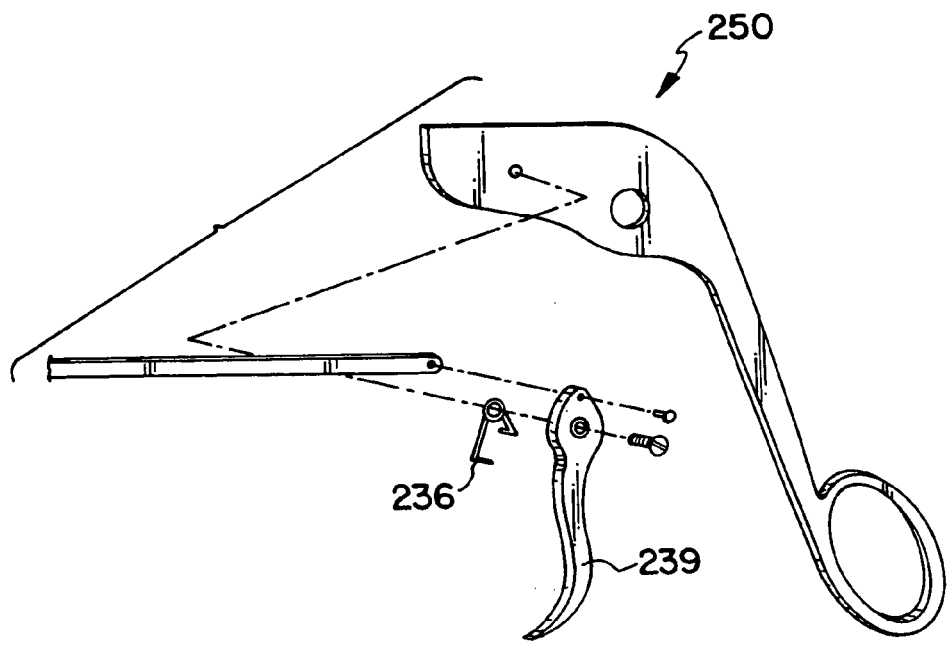
FIG. 15B is an exploded view of the trigger and a locking mechanism of FIG. 15A.

Referring to FIGS. 15A and 15B, in an alternate implementation, the trigger portion 250 includes a trigger mechanism 239, which is a hinged lever 239 attached to a push-pull rod 238 that ends in, e.g., one of the suture capture devices of FIGS. 14A-14H. A locking mechanism 236, such as a spring or ratchet-type lock is used to hold the suture capture device, e.g., suture pick or hook, in a retracted position and to retain the suture capture device in a suture holding position. After the needle 115 has passed through the tissue, the lever 239 is pulled towards the handle 190 by the surgeon's finger. This action advances the push/pull rod 238 forward. The suture capture device then captures the suture from the needle and holds it in the suture slot. When the surgeon releases lever 239, the locking mechanism acts to hold the suture capture device in its suture holding position. To release the suture, the lever 239 is actuated again to advance the push/pull rod 238 and release the suture.

Figures 15C, 15D:
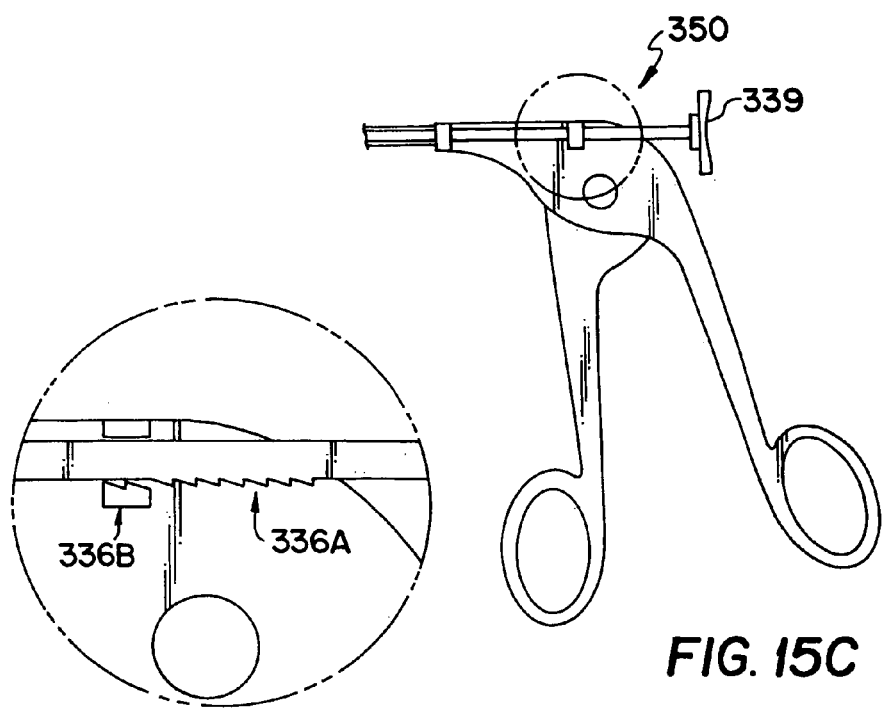
FIG. 15C is a side view of another alternative implementation of the trigger.
FIG. 15D is a detailed view of a locking mechanism of the trigger of FIG. 15C.

Referring to FIGS. 15C and 15D, in another alternative implementation, the trigger portion 350 includes a trigger mechanism 339 in the form of a button 339, and a push rod 338. The thumb-operated button 339 activates the push rod 338, which moves the suture grasper 130 in a forward direction to capture the suture with the suture capture device, e.g., suture capture device 232, after the articulating jaw 110 is closed and the suture needle 115 has penetrated the tissue. The button 339 is attached to the push rod 338 and the push rod 338 runs through a single or a series of rings 335 that direct the suture grasper 130 forward to grasp the suture. The articulating jaw 110 is then opened and removed from the tissue.

A locking mechanism 336 for the suture grasper 130 is provided to secure the suture grasper 130 in position once the suture grasper 130 has been activated to hold the suture in the suture slot 121. The locking mechanism can be a spring type mechanism that holds the suture capture device in a retracted position and retains the suture capture device in a suture holding position. Alternatively, as shown, the locking mechanism includes a plurality of teeth 336A that mate with a latch 336B, for example, within ring 335 (see FIG. 15D) or on the instrument handle 190 (not shown), in order to lock the suture grasper 130 in place. To release, the locking mechanism 336, button 339 is pushed away from the handle 190 to separate teeth 336A and latch 336B.

Referring to FIGS. 16A-16E, other implementations of the push/pull rod of the suture grasper include, for example, a dual split rod configuration 438 or a single rod configuration 538, 638, 738, 838. In the single rod configurations, the rod can have locking teeth 736, 836, as shown, for example, in FIGS. 16D and 16E. In each implementation, the rod is attached at its proximal end to a thumb-plate, for example, the button 339 of FIG. 15B or an articulating lever, for example, lever 239 of FIG. 15A.

Referring to FIGS. 17A-17H, an alternate implementation of a suture passing surgical instrument 1700 includes an elongated shaft 1740 with a distal portion 1705 and a proximal portion 1745. At the proximal end of the elongated shaft, there is a handle 1790, a control arm 1712, and a trigger portion 1750. At the distal end, there is a set of jaws 1718, 1720, a suture grasper 1730, and a moveable needle arm 1710.

The jaw 1718 is controlled by the handle 1790 and attached to the elongated shaft 1740 by a pivot hinge assembly 1765, as described above in relation to articulating jaw 110.

The needle arm 1710 is attached to a push/pull rod 1712A and includes a needle 1715 at its distal end. The push/pull rod 1712A runs along the elongated shaft 1740 and is actuated by a lever 1712 attached to the handle 1790. The surgeon activates the lever 1712 with his finger to move the needle arm 1710 forward and backward.

The suture grasper 1730 is controlled by the trigger portion 1750 and disposed on jaw 1720, which is similar to the tissue platform 120 described above. The trigger portion 1750 includes a trigger mechanism 1739, e.g., a thumb-operated button, and a rod 1738. The thumb-operated button 1739 is attached to the rod 1738, which runs along the elongated shaft 1740 to control the movement of the suture grasper 1730, as described above.

The trigger portion 1750 permits the surgeon to control when the surgeon captures the suture from the needle 1715, after the needle 1715 and the suture have been passed through the tissue and are exposed above the jaw 1720. As described above, the surgeon activates the button 1739 with his thumb to move the suture grasper 1730 forward to grasp the suture. The trigger portion may have similar alternatives and variations as previously described.

Referring to FIG. 17B, the push/pull rod 1728 includes two tabs 1728A, 1728B at its proximal end and moves along a groove 1740A of the instrument shaft 1740, as described above.

Referring to FIGS. 17C and 17D, the needle 1715 on the needle arm 1710 is shaped like a tapered rectangle that ends in a sharp tip 1713. The needle 1715 is formed of nitinol, hardened stainless steel, or similar materials. The needle 1715 optionally is formed integral to the needle arm 1710 or separately and then rigidly attached (i.e., welded or mounted) to the needle arm 1710.

The needle 1715 initially extends from the needle arm 1710, which is parallel to the pair of jaws 1718, 1720, and has a suture eyelet 1711 disposed therein. Needle arm 1710 is attached to push/pull rod 1712A at pivot 1710A. The suture eyelet 1711 is disposed proximate to the tip 1713 of the needle 1715. As described above, the suture eyelet 1711 can, for example, open to the front or side of the needle and have various alternative shapes.

An operator moves the needle arm 1710 to articulate away from the set of jaws 1718, 1720 in order for suture to be threaded onto the needle 1715. A "free" suture (not attached to anything) or suture attached to a soft tissue attachment device, e.g., an anchor is threaded through the suture eyelet 1711 of the needle 1715. The ability to use "free" suture with the suture passing surgical instrument provides a surgeon with the flexibility to use intricate weaving (suture) patterns without the demand of visualizing each suture transfer.

After suture is threaded through the needle 1715, an operator moves lever 1712 to return the needle arm 1710 parallel to the set of jaws 1718, 1720. Movement of the push/pull rod 1712A distally causes the needle arm 1710 to move distally until tip 1713 of needle 1715 contacts deflector 1718A of jaw 1718. Contact with deflector 1718A by needle 1715 causes needle 1715 to pivot towards jaw 1720 about pivot 1715A such that needle 1715 passes through passageway 1722B of jaw 1718 and passageway 1722A of jaw 1720.

Referring to FIG. 17E, the surface 1729 of the jaw 1720 (the surface that faces the jaw 1718) and the surface 1717 of the horizontal portion of the jaw 1718 (the surface facing the jaw 1720) can be smooth and/or serrated. The serrations 1723, 1724, respectively, can vary in shape, number, and length, as described above.

Referring to FIGS. 17F and 17G, the set of jaws 1718, 1720 (shown in these figures without grooves for clarity) includes passageways 1722A, 1722B through which the needle 1715 of the needle arm 1710 passes. Each passageway 1722A, 1722B is slightly wider than the needle 1715.

The passageway 1722A of the jaw 1720 includes two suture slots or grooves 1721X, 1721Y in which the suture rests after the needle 1715 has passed through the tissue. In this implementation, the grooves 1721X, 1721Y are provided in each lengthwise side 1722A1, 1722A2 of the passageway 1722A. The suture capture device 1732 moves the suture away from the needle 1715 and holds the suture for example in the suture slot 1721X against surface 1721A as described above.

Jaw 1718 includes passageway 1722B, which is defined by a central rectangular cutout. The Jaw 1718 can have similar grooves, as described above in relation to jaw 1720.

Jaw 1720 includes a U-shaped end 1720A defining passageway 1722A. A grasper guide 1770, as described above, is located on the jaw 1720.

Referring to FIGS. 17A and 17H, suture grasper 1730 is disposed on jaw 1720 and has similar alternatives as those described above.

Figure 18A:
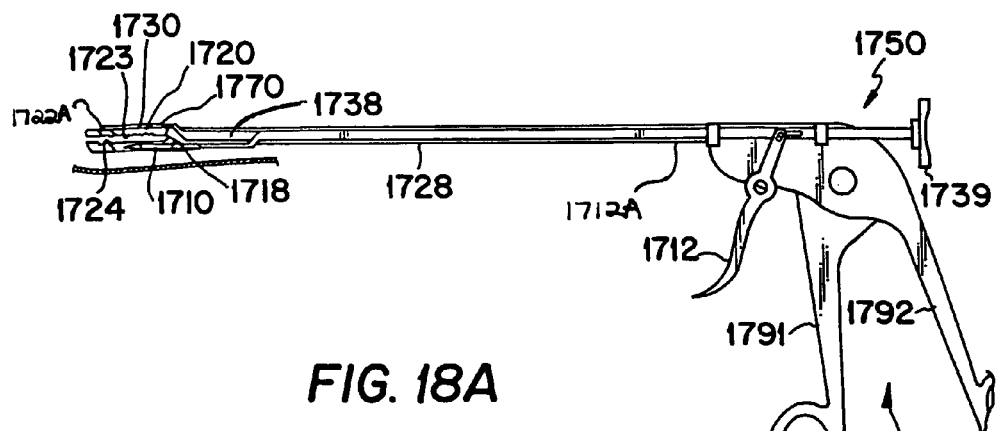
FIGS. 18A-18E illustrate use of the surgical instrument of FIG. 17.
Figure 18B:
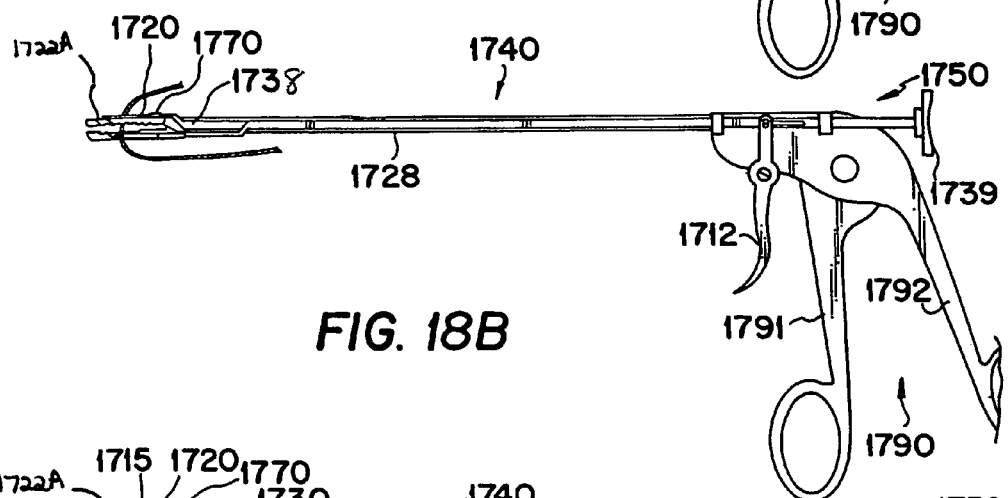
Figure 18C:
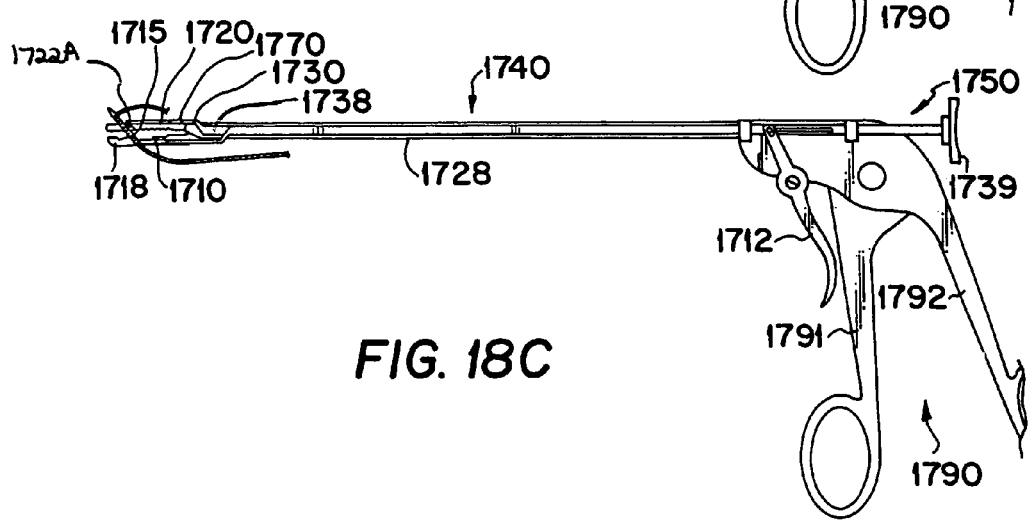
Figure 18D:
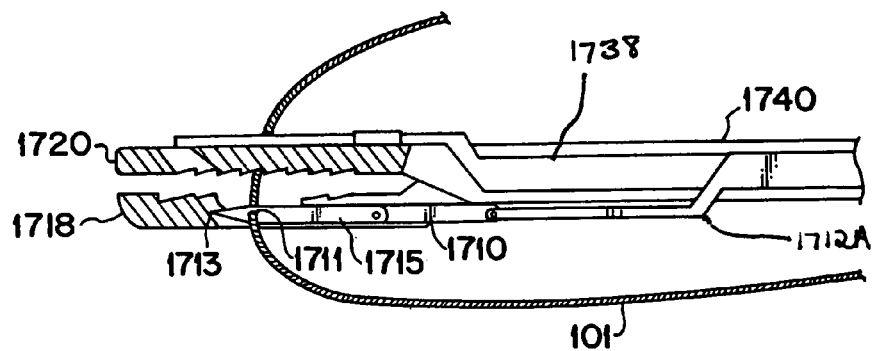

Referring to FIGS. 18A-18E, an operator uses the suture passing surgical instrument 1700 of FIG. 17A as follows. In the position of instrument 1700 as shown in FIG. 18A, the operator has moved lever 1712 to move moveable needle arm 1710 of the suture passing surgical instrument 1700 away from the set of jaws 1718, 1720 to load suture through eyelet 1711. Then, the operator moves lever 1712 to return needle arm 1710 parallel to the set of jaws 1718, 1720, as shown in FIGS. 18B and 18D.

The operator places instrument 1700 in the surgical site through a cannula (not shown) to the surgical site. The operator moves handle 1790 to articulate jaw 1718 of the set of jaws 1718, 1720 such that the jaws 1718, 1720 open and close to grasp tissue therebetween.

Figure 18E:
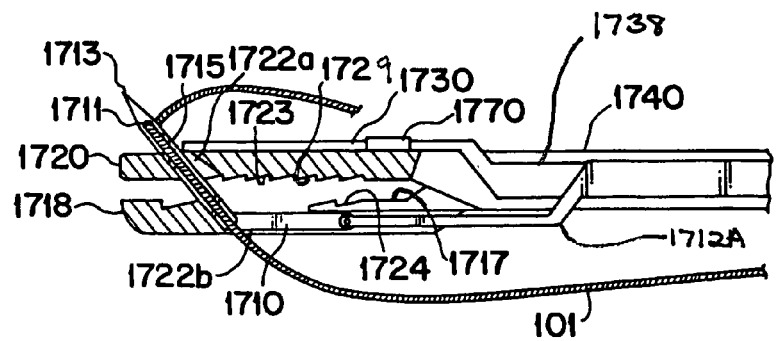

The operator moves lever 1712 to move moveable needle arm 1710 distally toward the deflector 1718A of jaw 1718. Upon contacting deflector 1718A, moveable needle arm 1710 pivots about pivot 1715A toward jaw 1720 and pierces the tissue held by the jaws 1718, 1720 through passageway 1722A, 1722B, as shown in FIGS. 18C and 18E.

Next, the operator activates trigger portion 1750 to advance suture grasper 1730 distally to hold the suture in suture slot 1721X. The operator moves lever 1712 to move needle arm 1710 back out of the set of jaws 1718, 1720. The needle 1715 moves out of the tissue through passageway 1722A, 1722B. The operator then moves the lever 1712 to return the needle arm 1710 parallel to the set of jaws 1718, 1720.

The operator moves handle 1790 to open the set of jaws 1718, 1720 to release the tissue and then the operator moves handle 1790 to close the jaws 1718, 1720. The free end of the suture remains above the jaw 1720. The other end of the suture is located in the suture slot 1721X and through the tissue. The operator removes instrument 1700 from the surgical site. The instrument may be rethreaded and reinserted through the cannula to the surgical site in order to pass suture multiple times.

A number of implementations have been described. Nevertheless, it will be understood that various modifications may be made without departing from the spirit and scope. For example, the tissue platform may include one suture slot or the needle may pass through tissue to either side of the articulating jaw or set of jaws. Alternatively, the passageway may be offset to accommodate orientation of the needle or suture eyelet. The suture capture device may be or may include a latch or a cutout. The trigger portion may include a button or other mechanism to activate movement of the suture grasper. The needle may be formed separately from the jaw and then rigidly attached, e.g., welded or mounted to the jaw. The eyelet of the needle may open to the front of the needle or to the inside of the needle.

Additionally, the instrument can be used in many surgical environments, including, for example, open, mini-open, and endoscopic, and with visualization, limited visualization, or no visualization of the suture grasper. Also, other devices for attaching tissue to bone or tissue to tissue will work with the device and can be carried into the operative site and attached or secured by the device. The type of material used, i.e., material construction, braided or monofilament or combinations of construction and material type, synthetic, natural, permanent or reabsorbable, can vary, and a variety of material diameters are possible. Loose or highly mobile tissue can be translocated as desired by the surgeon. Also, the same suture strand can be passed through tissue multiple times and in various directions. Accordingly, other implementations are within the scope of the following claims.

What is claimed is:

1. A surgical instrument comprising:
a first member adapted to receive suture;
a second member coupled to the first member such that the first member and the second member are configured for motion relative to each other between a first spaced position, in which tissue can be received therebetween, and a second position, in which the first member is configured to pass the suture through the tissue;
a grasper coupled to the second member and configured for movement along a longitudinal axis of the second member to engage the suture, when the first member and second member are in the second position, such that the grasper holds the suture when the first member and the second member are returned to the first spaced position; and
a trigger portion that includes a trigger mechanism and a spring, the trigger mechanism being configured to rotate about the longitudinal axis of the second member from a first position in which the grasper does not engage the suture to a second position in which a force from the spring pushes the suture grasper move along the longitudinal axis of the second member to engage the suture.

2. The surgical instrument of claim 1 wherein the second member defines a slot for receiving suture from the first member, and the grasper is configured to trap suture within the slot to hold the suture when the first member and the second member are returned to the first spaced position.

3. The surgical instrument of claim 1 wherein the second member defines a passageway for receiving a portion of the first member.

4. The surgical instrument of claim 3 wherein the second member defines a slot for receiving suture from the first member, the slot opening into the passageway.

5. The surgical instrument of claim 1 wherein the first member includes a needle for piercing tissue.

6. The surgical instrument of claim 5 wherein the needle defines an eyelet.

7. The surgical instrument of claim 5 wherein the needle defines two eyelets.

8. The surgical instrument of claim 6 wherein the eyelet comprises a cutout.

9. The surgical instrument of claim 1, the instrument further comprising a handle for controlling movement of the first member.

10. The surgical instrument of claim 9 wherein the handle comprises an articulating handle and a stationary handle.

11. The surgical instrument of claim 1 wherein the first member comprises a jaw and a needle arm extending from a distal end of the surgical instrument, the needle arm being adapted to receive suture.

12. The surgical instrument of claim 1 wherein the second member defines a passageway, the passageway being configured to receive a portion of the needle arm.

13. The surgical instrument of claim 12 wherein the second member includes at least one suture slot, the at least one suture slot is disposed in a lengthwise side of the passageway and opens to the passageway.

14. The surgical instrument of claim 1 wherein the grasper is disposed on a portion of the second member.

15. The surgical instrument of claim 1 wherein the grasper comprises a hook.

16. The surgical instrument of claim 1 wherein the grasper comprises a wedge.

17. The surgical instrument of claim 1 wherein the grasper comprises a set of jaws.

18. The surgical instrument of claim 1 wherein the grasper comprises a U-shaped cup.

19. The surgical instrument of claim 1 wherein the trigger mechanism comprises a paddle.

20. The surgical instrument of claim 1 further comprising a grasper guide, the grasper guide being disposed on a portion of the second member.

21. The surgical instrument of claim 20 wherein the trigger portion moves the grasper distally under the grasper guide to engage the suture.

22. The surgical instrument of claim 1 wherein a portion of the first member is serrated.

23. The surgical instrument of claim 1 wherein a portion of the second member is serrated.

24. The surgical instrument of claim 1, wherein the trigger portion further includes a rigid pin configured to follow a J-shaped groove in the trigger mechanism.

25. The surgical instrument of claim 24, wherein, when the grasper is in the first position, the rigid pin is positioned in a hook side of the J-shaped groove, and, when the trigger mechanism is rotated about the axis of the grasper to the second position, the rigid pin is moved to a long side of the J-groove.

26. The surgical instrument of claim 1, wherein the trigger portion further includes a spring plate coupled to the grasper, the trigger mechanism being further configured to compress the spring when in the second position such that the force from the spring pushes against the spring plate and thereby pushes the suture grasper along the longitudinal axis of the second member to engage the suture.

* * * * *